US009428487B2

(12) United States Patent
Bretschneider et al.

(10) Patent No.: US 9,428,487 B2
(45) Date of Patent: Aug. 30, 2016

(54) HETEROAROMATIC AMIDES AND THIOAMIDES AS PESTICIDES

(75) Inventors: Thomas Bretschneider, Lohmer (DE);
Eva-Maria Franken, Leichlingen (DE);
Ulrich Görgens, Ratingen (DE);
Martin Fusslein, Düsseldorf (DE);
Achim Hense, Leverkusen (DE);
Joachim Kluth, Langenfeld (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 12/997,803

(22) PCT Filed: Jun. 4, 2009

(86) PCT No.: PCT/EP2009/003984
§ 371 (c)(1),
(2), (4) Date: Dec. 13, 2010

(87) PCT Pub. No.: WO2009/149858
PCT Pub. Date: Dec. 17, 2009

(65) Prior Publication Data
US 2011/0098287 A1 Apr. 28, 2011

(30) Foreign Application Priority Data
Jun. 13, 2008 (EP) ..................... 08158247

(51) Int. Cl.
*C07D 401/04* (2006.01)
*C07D 401/14* (2006.01)
*C07D 417/04* (2006.01)
*C07D 417/14* (2006.01)

(52) U.S. Cl.
CPC ........... *C07D 401/14* (2013.01); *C07D 401/04* (2013.01); *C07D 417/04* (2013.01); *C07D 417/14* (2013.01)

(58) Field of Classification Search
CPC C07D 401/14; C07D 401/04; C07D 417/04; C07D 417/14
USPC ......................... 546/20.4; 504/252
See application file for complete search history.

(56) References Cited

U.S. PATENT DOCUMENTS

| 4,080,457 | A | 3/1978 | Harrison et al. | |
| 4,260,765 | A * | 4/1981 | Harrison et al. | 546/270.4 |
| 2002/0013326 | A1 | 1/2002 | Tiebes et al. | |
| 2002/0042428 | A1* | 4/2002 | Myers et al. | 514/305 |
| 2003/0018192 | A1 | 1/2003 | Meudt et al. | |
| 2007/0259919 | A1 | 11/2007 | Rheinheimer et al. | |
| 2009/0030024 | A1 | 1/2009 | Greul et al. | |
| 2012/0094837 | A1 | 4/2012 | Mühlthau et al. | |
| 2012/0095023 | A1 | 4/2012 | Bretschneider et al. | |

FOREIGN PATENT DOCUMENTS

| CN | 101711245 A | | 5/2010 |
| DE | 2 221 647 | | 11/1972 |
| EP | 0 030 092 A1 | | 6/1981 |
| EP | 0 334 146 A1 | | 3/1989 |
| EP | 1 270 535 A2 | | 2/2003 |
| WO | WO 98/57969 A1 | | 12/1998 |
| WO | WO 99/62885 A1 | | 12/1999 |
| WO | WO 02/17358 A2 | | 2/2002 |
| WO | WO 02/066469 | * | 8/2002 |
| WO | WO 03/018585 A1 | | 3/2003 |
| WO | WO 2004/002409 A2 | | 1/2004 |
| WO | WO 2004/016741 A2 | | 2/2004 |
| WO | WO 2005/090328 A1 | | 9/2005 |
| WO | WO 2006/000358 A1 | | 1/2006 |
| WO | WO 2006/062224 A1 | | 6/2006 |
| WO | WO 2006/127550 | * | 11/2006 |
| WO | WO 2007/033780 A2 | | 3/2007 |
| WO | WO 2009/012482 | | 1/2009 |

OTHER PUBLICATIONS

Registry No. 948643-91-2, STN file registry, Sep. 28, 2007.*
Registry No. 948709-09-9, STN file registry, Sep. 28, 2007.*
Registry No. 948741-74-0, STN file registry, Sep. 28, 2007.*
Registry No. 1087424-16-5, STN file registry, Dec. 21, 2008.*
RN 948741-78-4, STN, file Registry, Sep. 28, 2007.*
RN 948708-53-0, STN, File Registry, Sep. 28, 2007.*
Bradley, P., et al., "Preliminary communication: The synthesis of new mesogenic 1,3,4-thiadiazole-2-carboxylate esters via a novel ring-closure," *Liquid Crystals Today* 14(1):15-18, Taylor & Francis Group Ltd., England (2005).
Bracher, F. and Papke, T., "Total Syntheses and Antimicrobial Activities of Pyridine Alkaloids Rubiaceae," *Monatshefte für Chemie* 126:805-809, Springer-Verlag, Germany (1995).
Cai, D., et al., "Effective lithiation of 3-bromopyridine: synthesis of 3-pyridine boronic acid and variously 3-substituted pyridines," *Tetrahedron Letters* 43: 4285-4287, Elsevier Science Ltd., England (2002).
Chang, K.Y., et al., "Synthesis and Structure-Activity Relationships of Quaternary Ammonium Cephalosporins with 3-Pyrazolylpyridinium Derivatives," *Bioorg. Med. Chem. Lett* 10(11):1211-1214, Elsevier Science Ltd., England (2000).
Denton, T.T., et al., "5-Substituted, 6-Substituted, and Unsubstituted 3-Heteroaromatic Pyridine Analogues of Nicotine as Selective Inhibitors of Cytochrome P-450 2A6," *J Med Chem.* 48(1):224-39, American Chemical Society, United States (2005).
Gough, A.C. and King, H., "4-Nitro-5-(3-pyridyl)pyrazole, a New Oxidation Product of Nicotine. Part III Confirmatory Synthetical Experiments," *J. Chem. Soc.* pp. 350-351 (1933).

(Continued)

*Primary Examiner* — Rebecca Anderson
(74) *Attorney, Agent, or Firm* — Sterne, Kessler, Goldstein, Fox P.L.L.C.

(57) ABSTRACT

The present application relates to novel amides and thioamides, to processes for preparation thereof and to use thereof for controlling animal pests, in particular arthropods and especially insects.

7 Claims, No Drawings

(56) References Cited

OTHER PUBLICATIONS

Ishiyama, T., et al., "Synthesis of pinacol arylboronates via cross-coupling reaction of bis(pinacolato)diboron with chloroarenes catalyzed by palladium(0)-tricyclohexylphosphine complexes," *Tetrahedron* 57(49):9813-9816, Elsevier Science Ltd., England (2001).
Jensen, M.S., et al., "Efficient Synthesis of a $GABA_A$ $\alpha_{2,3}$-Selective Allosteric Modulator via a Sequential Pd-Catalyzed Cross-Coupling Approach," *J. Org. Chem.* 70(15):6034-6039, American Chemical Society, United States (2005).
Lee, L.F., et al.,"Syntheses and Reactions of 2-Halo-5-thiazolecarboxylates," *J. Heterocyclic Chem.* 22:1621-1630, Journal of Heterocyclic Chemistry, United States (1985).
Li, W., et al., "An Improved Protocol for the Preparation of 3-pyridyl- and Some Arylboronic Acids," *J. Org. Chem*.67:5394-5397, American Chemical Society, United States (2002).
Manaka, A. and Sato, M., "Synthesis of Aromatic Thioamide from Nitrile without Handling of Gaseous Hydrogen Sulfide," *Synthetic Communications* 35:761-764, Taylor & Francis, England (2005).
Nishikawa, Y., et al., "Acrylamide Derivatives as Antiallergic Agents. 2. Synthesis and Structure-Activity Relationships of *N*-[4[4-(Diphenylmethyl)-1 piperazinyl]butyl]-3-(3-pyridyl)acrylamides," *J. Med. Chem.* 32(3):583-593, American Chemical Society, United States (1989).
Vallin, K.S., et al., "Aqueous DMF-Potassium Carbonate as a Substitute for Thallium and Silver Additives in the Palladium-Catalyzed Conversion of Aryl Bromides to Acetyl Arenes," *J. Org. Chem*.66(12):4340-4343, American Chemical Society, United States (Jun. 2001).
English language Abstract of European Patent No. EP 0 334 146 A1, espacenet database—worldwide, (2010).
English Language Abstract of International Patent No. WO 2005/090328 A1, espacenet database—worldwide, (2010).
International Search Report with Written Opinion for International Application No. PCT/EP2009/003984, European Patent Office, Netherlands, mailed on Oct. 27, 2009.
Wislicenus, W., "Über Ester-Kondensationen mit Chlor-essigester," *Chem. Ber.* 43:3528-3533, Deutsche Chemische Gesellschaft, Germany (1910).
Erlenmeyer, H., et al., "Über Derivate con Thiazolcarbonsäuren," *Helvetica Chimica Acta* Verlag Helvetica Chimica Acta AG, Germany (1944).
Notice of Allowance mailed Apr. 10, 2014, in U.S. Appl. No. 13/054,401, inventors Bretschneider et al., filed May 17, 2011.
Office Action mailed Aug. 28, 2013 in U.S. Appl. No. 13/054,401, inventors Bretschneider et al., filed May 17, 2011.
Advisory Action mailed Sep. 18, 2013 in U.S. Appl. No. 13/183,709, inventors Mülthau et al., filed Jul. 15, 2011.
Office Action mailed May 22, 2013, in U.S. Appl. No. 13/183,709, inventors Mülthau et al., filed Jul. 15, 2011.
Office Action mailed Oct. 3, 2012, in U.S. Appl. No. 13/183,709, inventors Mülthau et al., filed Jul. 15, 2011.
Office Action mailed Apr. 22, 2013, in U.S. Appl. No. 13/088,026, inventors Bretschneider et al., filed Apr. 15, 2011.
Office Action mailed Dec. 24, 2013, in U.S. Appl. No. 13/183,709, inventors Mülthau et al., filed Jul. 15, 2011.
Notice of Allowance mailed Oct. 16, 2013, in U.S. Appl. No. 13/088,026, inventors Bretschneider et al., filed Apr. 15, 2011.
Office Action mailed Jan. 11, 2013, in U.S. Appl. No. 13/054,401, inventors Bretschneider et al., filed May 17, 2011.
Office Action mailed Dec. 13, 2013, in U.S. Appl. No. 13/054,401, inventors Bretschneider et al., filed May 17, 2011.
Office Action mailed Jul. 29, 2015 in U.S. Appl. No. 14/156,897, Bretschneider, T., et al., filed Jan. 16, 2014.
Office Action mailed Jan. 27, 2016 in U.S. Appl. No. 14/327,144, Bretschneider, T., et al., filed Jul. 9, 2014.
Notice of Allowance mailed Feb. 23, 2016 in U.S. Appl. No. 14/156,897, Bretschneider, T., et al., filed Jan. 16, 2014.

* cited by examiner

HETEROAROMATIC AMIDES AND THIOAMIDES AS PESTICIDES

The present application relates to novel amides and thioamides, to processes for preparation thereof and to use thereof for controlling animal pests, which include arthropods and especially insects.

Particular amides have already become known as insecticidally active ingredients (cf. DE 2221647).

Modern crop protection compositions have to satisfy many demands, for example in relation to efficacy, persistence and spectrum of their action, and possible use. Important questions relate to toxicity, combinability with other active ingredients or formulating assistants, and another is that of the effort and expense of synthesizing an active ingredient. Moreover, resistances can occur. For all these reasons, the search for novel crop protection compositions cannot be considered to be complete, and there is a constant need for novel compounds with improved properties over the known compounds, at least in relation to individual aspects.

It was an object of the present invention to provide compounds by which the spectrum of crop protection compositions is broadened in various respects.

The object, and also further objects which are not stated explicitly and are derivable or discernible from the connections discussed herein, are achieved by novel compounds of the formula (I)

in which
(Ia)
$G^1$ is N or C-halogen, and
$G^2$ is a radical from the group of (A)

(B) and (C)

in which
$R^1$ is hydrogen or alkyl and
$G^3$ is $C(=X)NR^2R^3$
in which
X is oxygen or sulphur,
$R^2$ is a radical from the group of hydrogen, alkyl, haloalkyl, alkoxy, haloalkoxy, alkenyl, alkoxyalkyl, optionally halogen-substituted alkylcarbonyl, optionally halogen-substituted alkoxycarbonyl and optionally halogen-substituted cycloalkylcarbonyl,
and
$R^3$ is a radical from the group of hydrogen, alkyl, haloalkyl, cyanoalkyl, alkenyl, haloalkenyl, alkynyl, haloalkynyl, alkoxy, haloalkoxy, optionally halogen-substituted alkoxyalkyl, optionally halogen-substituted bis(alkoxy)alkyl, optionally halogen-substituted alkylthioalkyl, optionally halogen-substituted alkylcarbonylalkyl, optionally halogen-substituted alkylsulphinylalkyl, optionally halogen-substituted alkylsulphonylalkyl, optionally halogen-substituted alkoxycarbonylalkyl, alkynyloxy, alkynyloxycarbonyl, optionally substituted cycloalkyl, optionally substituted cycloalkylcarbonyl, optionally substituted cycloalkylalkyl, optionally substituted heterocyclyl, optionally substituted heterocyclylalkyl, optionally substituted arylalkyl, optionally substituted hetarylalkyl and $NR^4R^5$ in which $R^4$ and $R^5$ are each independently a radical from the group of hydrogen, alkyl, haloalkyl, cycloalkyl, alkoxy, alkylcarbonyl, alkoxycarbonyl, hetaryl and heterocyclyl, or $R^4$ and $R^5$ together with the nitrogen atom to which they are bonded form an optionally substituted heterocycle,
or
$R^2$ and $R^3$ together with the nitrogen atom to which they are bonded form an optionally substituted ring which optionally contains further heteroatoms,
or
(Ib)
in which
$G^1$ is CH and
$G^2$ is (B)

or (C)

in which
$R^1$ is hydrogen or alkyl and
$G^3$ is $C(=X)NR^2R^3$
in which
X is oxygen or sulphur,
$R^2$ is as defined above and
$R^3$ is as defined above or
$R^2$ and $R^3$ together with the nitrogen atom to which they are bonded form an optionally substituted ring which optionally contains further heteroatoms
or
(Ic)
in which
$G^1$ is CH, G² is

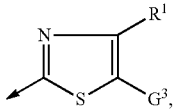
(A)

R¹ is hydrogen or alkyl and
G³ is C(=S)NR²R³,
in which
R² is as defined above and
R³ is as defined above or
R² and R³ together with the nitrogen atom to which they are bonded form an optionally substituted ring which optionally contains further heteroatoms
or
(Id)
in which
G¹ is CH and
G² is

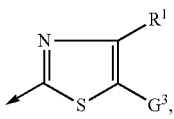
(A)

R¹ is hydrogen or alkyl and
G³ is C(=O)NR²R³
in which
R² is a radical from the group of hydrogen, alkyl, haloalkyl, alkoxy, haloalkoxy, alkenyl, alkoxyalkyl, optionally halogen-substituted alkylcarbonyl, optionally halogen-substituted alkoxycarbonyl and optionally halogen-substituted cycloalkylcarbonyl,
and
R³ is a radical from the group of haloalkyl, cyanoalkyl, haloalkenyl, haloalkynyl, alkoxy, haloalkoxy, halogen-substituted alkoxyalkyl, optionally halogen-substituted bis(alkoxy)alkyl, optionally halogen-substituted alkylthioalkyl, optionally halogen-substituted alkylcarbonylalkyl, optionally halogen-substituted alkylsulphinylalkyl, optionally halogen-substituted alkylsulphonylalkyl, optionally halogen-substituted alkoxycarbonylalkyl, alkynyloxy, alkynyloxycarbonyl, halogen-, cyano-, alkyl-, haloalkyl-, alkoxy-, haloalkoxy-, alkoxycarbonyl-, haloalkoxycarbonyl- or hetaryl-substituted (where hetaryl may itself be substituted by alkyl or halogen) cycloalkyl, optionally substituted cycloalkylcarbonyl, optionally substituted cycloalkylalkyl, optionally substituted heterocyclyl, optionally substituted heterocyclylalkyl, halogen-, cyano-, alkyl-, haloalkyl-, alkoxy- or haloalkoxy-substituted arylalkyl, optionally substituted hetarylalkyl and NR⁴R⁵ in which R⁴ and R⁵ are each independently a radical from the group of hydrogen, alkyl, haloalkyl, cycloalkyl, alkoxy, alkylcarbonyl, alkoxycarbonyl, hetaryl and heterocyclyl, or R⁴ and R⁵ together with the nitrogen atom to which they are bonded form an optionally substituted heterocycle
or
(Ie)
in which
G¹ is CH and G² is

(A)

R¹ is hydrogen and
G³ is C(=O)NR²R³,
in which
R² is hydrogen or alkyl
and
R³ is hydrogen or alkyl,
and salts and N-oxides of the compounds of the formula (I).
More particularly, the abovementioned problem, and also further objects which are not stated explicitly and are derivable or discernible from the connections discussed herein, are achieved by novel compounds of the abovementioned formula (I), in which
(Ia)
G¹ is N or C-halogen, and
G² is a radical from the group of

(A)

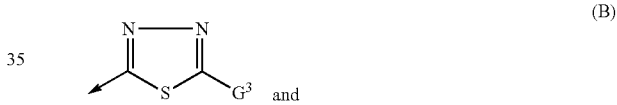
(B) and

(C)

in which
R¹ is hydrogen or alkyl and
G³ is C(=X)NR²R³,
in which
X is oxygen or sulphur,
R² is a radical from the group of hydrogen, alkyl, haloalkyl, alkoxy, haloalkoxy, alkenyl, alkoxyalkyl, optionally halogen-substituted alkylcarbonyl, optionally halogen-substituted alkoxycarbonyl and optionally halogen-substituted cycloalkylcarbonyl,
and
R³ is a radical from the group of hydrogen, alkyl, haloalkyl, cyanoalkyl, alkenyl, haloalkenyl, alkynyl, haloalkynyl, alkoxy, haloalkoxy, optionally halogen-substituted alkoxyalkyl, optionally halogen-substituted bis(alkoxy)alkyl, optionally halogen-substituted alkylthioalkyl, optionally halogen-substituted alkylcarbonylalkyl, optionally halogen-substituted alkylsulphinylalkyl, optionally halogen-substituted alkylsulphonylalkyl, optionally halogen-substituted alkoxycarbonylalkyl, alkynyloxy, alkynyloxycarbonyl, optionally halogen-, cyano-, alkyl-, haloalkyl-, alkoxy-, haloalkoxy-, alkoxycarbonyl-, haloalkoxycarbonyl- or hetaryl-substituted (where hetaryl may itself be substituted by alkyl or halogen) cycloalkyl, optionally halogen-, cyano-, alkyl-, haloalkyl-, alkoxy-, haloalkoxy-, alkoxycarbonyl-, haloalkoxycarbonyl- or hetaryl-substituted (where hetaryl may itself be substituted by alkyl or halogen) cycloalkylcarbonyl, optionally halogen-, cyano-, alkyl-, haloalkyl-, alkoxy-, haloalkoxy-, alkoxycarbonyl-, haloalkoxycarbonyl- or hetaryl-substituted (where hetaryl may itself be substituted by alkyl or halogen) cycloalkylalkyl, optionally substituted heterocyclyl, optionally halogen-, cyano- (including in the alkyl moiety), nitro-, alkyl-, haloalkyl-, cycloalkyl-, alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, alkylcycloalkyl-, cycloalkylalkyl-, alkylcarbonyl-, alkoxycarbonyl- or aminocarbonyl-substituted heterocyclylalkyl, optionally halogen-, cyano-, alkyl-, haloalkyl-, alkoxy- or haloalkoxy-substituted arylalkyl, optionally halogen-, cyano- (including in the alkyl moiety), nitro-, alkyl-, haloalkyl-, cycloalkyl-, alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, alkylcycloalkyl-, alkylcarbonyl-, alkoxycarbonyl- or aminocarbonyl-substituted hetarylalkyl and NR$^4$R$^5$ in which R$^4$ and R$^5$ are each independently a radical from the group of hydrogen, alkyl, haloalkyl, cycloalkyl, alkoxy, alkylcarbonyl, alkoxycarbonyl, hetaryl and heterocyclyl, or R$^4$ and R$^5$ together with the nitrogen atom to which they are bonded form an optionally substituted heterocycle, or R$^2$ and R$^3$ together with the nitrogen atom to which they are bonded form an optionally substituted ring which optionally contains further heteroatoms, or (Ib)

in which

G$^1$ is CH and

G$^2$ is

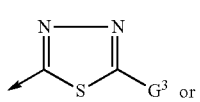

(B)

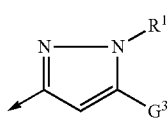

(C)

in which

R$^1$ is hydrogen or alkyl and

G$^3$ is C(=X)NR$^2$R$^3$, in which

X is oxygen or sulphur,

R$^2$ is as defined above and

R$^3$ is as defined above or

R$^2$ and R$^3$ together with the nitrogen atom to which they are bonded form an optionally substituted ring which optionally contains further heteroatoms or (Ic)

in which

G$^1$ is CH,

G$^2$ is

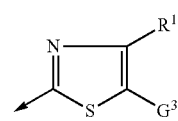

(A)

R$^1$ is hydrogen or alkyl and

G$^3$ is C(=S)NR$^2$R$^3$ in which

R$^2$ is as defined above and

R$^3$ is as defined above or

R$^2$ and R$^3$ together with the nitrogen atom to which they are bonded form an optionally substituted ring which optionally contains further heteroatoms or (Id)

in which

G$^1$ is CH and

G$^2$ is

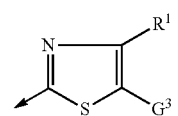

(A)

R$^1$ is hydrogen or alkyl and

G$^3$ is C(=O)NR$^2$R$^3$ in which

R$^2$ is a radical from the group of hydrogen, alkyl, haloalkyl, alkoxy, haloalkoxy, alkenyl, alkoxyalkyl, optionally halogen-substituted alkylcarbonyl, optionally halogen-substituted alkoxycarbonyl and optionally halogen-substituted cycloalkylcarbonyl, and R$^3$ is a radical from the group of haloalkyl, cyanoalkyl, haloalkenyl, haloalkynyl, alkoxy, haloalkoxy, halogen-substituted alkoxyalkyl, optionally halogen-substituted bis(alkoxy)alkyl, optionally halogen-substituted alkylthioalkyl, optionally halogen-substituted alkylcarbonylalkyl, optionally halogen-substituted alkylsulphinylalkyl, optionally halogen-substituted alkylsulphonylalkyl, optionally halogen-substituted alkoxycarbonylalkyl, alkynyloxy, alkynyloxycarbonyl, halogen-, cyano-, alkyl-, haloalkyl-, alkoxy-, haloalkoxy-, alkoxycarbonyl-, haloalkoxycarbonyl- or hetaryl-substituted (where hetaryl may itself be substituted by alkyl or halogen) cycloalkyl, optionally halogen-, cyano-, alkyl-, haloalkyl-, alkoxy-, haloalkoxy-, alkoxycarbonyl-, haloalkoxycarbonyl- or hetaryl-substituted (where hetaryl may itself be substituted by alkyl or halogen) cycloalkylcarbonyl, optionally halogen-, cyano-, alkyl-, haloalkyl-, alkoxy-, haloalkoxy-, alkoxycarbonyl-, haloalkoxycarbonyl- or hetaryl-substituted (where hetaryl may itself be substituted by alkyl or halogen) cycloalkylalkyl, optionally substituted heterocyclyl, optionally halogen-, cyano- (including in the alkyl moiety), nitro-, alkyl-, haloalkyl-, cycloalkyl-, alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, cycloalkylalkyl-, alkylcycloalkyl-, alkylcarbonyl-, alkoxycarbonyl- or aminocarbonyl-substituted heterocyclylalkyl, halogen-, cyano-, alkyl-, haloalkyl-, alkoxy- or haloalkoxy-substituted arylalkyl, optionally halogen-, cyano- (including in the alkyl moiety), nitro-, alkyl-, haloalkyl-, cycloalkyl-, alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, alkylcycloalkyl-, alkylcarbonyl-, alkoxycarbonyl- or aminocarbonyl-substituted hetarylalkyl and NR⁴R⁵ in which R⁴ and R⁵ are each independently a radical from the group of hydrogen, alkyl, haloalkyl, cycloalkyl, alkoxy, alkylcarbonyl, alkoxycarbonyl, hetaryl and heterocyclyl, or R⁴ and R⁵ together with the nitrogen atom to which they are bonded form an optionally substituted heterocycle or
(Ie)
in which
G¹ is CH and
G² is

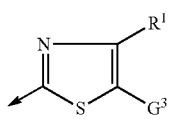

(A)

R¹ is hydrogen and
G³ is C(=O)NR²R³,
in which
R² hydrogen or alkyl
and
R³ is hydrogen or alkyl,
and salts and N-oxides of the compounds of the formula (I).

Moreover, it has been found that the novel compounds of the formula (I) in which G² is the (A) radical and X is oxygen are obtained when compounds of the formula (IIa)

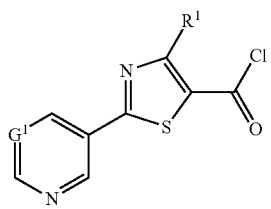

(IIa)

in which
G¹ and R¹ are each as defined above
are reacted with compounds of the formula (III)

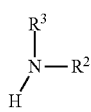

(III)

in which
R² and R³ are each as defined above,
optionally in the presence of a suitable diluent and optionally in the presence of a base (method 1),
that, in addition, the novel compounds of the formula (I) in which G² is the (B) radical and X is oxygen are obtained when
compounds of the formula (IIb)

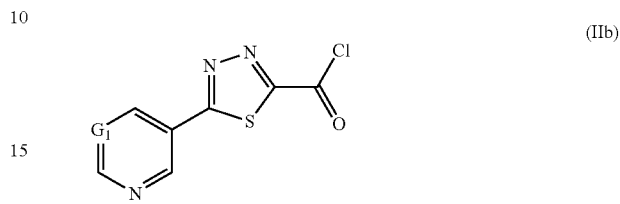

(IIb)

in which
G¹ is as defined above
are reacted with compounds of the formula (III)

(III)

in which
R² and R³ are each as defined above,
optionally in the presence of a suitable diluent and optionally in the presence of a base (method 2),
and that, in addition, the novel substituted compounds of the formula (I) in which G² is the (C) radical and X is oxygen are obtained when
compounds of the formula (IIc)

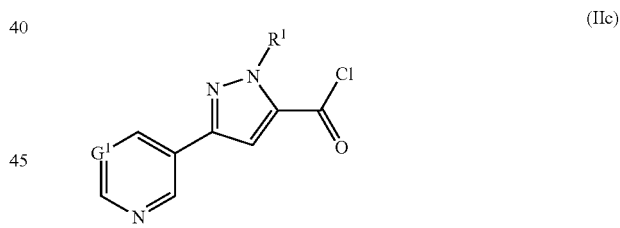

(IIc)

in which
G¹ and R¹ are each as defined above
are reacted with compounds of the formula (III)

(III)

in which
R² and R³ are each as defined above,
optionally in the presence of a suitable diluent and optionally in the presence of a base (method 3).

The compounds of the formula (I) obtainable by these methods can be converted to compounds of the formula (I) by reaction with a sulphurizing reagent in which X is sulphur.

Finally, it has been found that the novel compounds of the formula (I) possess very marked biological properties and are suitable in particular for control of animal pests, especially of insects, arachnids and nematodes, which occur in agriculture, in forests, in protection of stored products and materials, and in the hygiene sector.

Depending on the type of substituents, the compounds of the formula (I) may optionally be present in the form of geometric and/or in the form of optically active isomers or corresponding isomer mixtures in different compositions. The invention relates both to the pure isomers and to the isomer mixtures.

The inventive compounds may also be present in the form of metal complexes, as described for other amides, for example, in DE 2221647.

Preferred substituents and ranges of the radicals listed in the aforementioned compounds (Ia), (Ib) and (Ic) are illustrated hereinafter.

$R^1$ is hydrogen or $C_1$-$C_6$-alkyl, especially hydrogen or methyl.

$R^2$ is hydrogen, $C_1$-$C_6$-alkyl, $C_1$-$C_6$-haloalkyl, $C_1$-$C_4$-alkoxy, $C_1$-$C_4$-haloalkoxy, $C_2$-$C_4$-alkenyl, $C_1$-$C_4$-alkoxy-$C_1$-$C_4$-alkyl, optionally halogen-substituted $C_1$-$C_4$-alkylcarbonyl, optionally halogen-substituted $C_1$-$C_4$-alkoxycarbonyl or optionally halogen-substituted $C_3$-$C_6$-cycloalkylcarbonyl.

$R^3$ is hydrogen, $C_1$-$C_6$-alkyl, $C_1$-$C_6$-haloalkyl, cyano-$C_1$-$C_6$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_6$-alkoxy, $C_1$-$C_6$-haloalkoxy, optionally halogen-substituted $C_1$-$C_6$-alkoxy-$C_1$-$C_6$-alkyl, optionally halogen-substituted bis($C_1$-$C_6$-alkoxy)-$C_1$-$C_6$-alkyl, optionally halogen-substituted $C_1$-$C_6$-alkylthio-$C_1$-$C_6$-alkyl, optionally halogen-substituted $C_1$-$C_4$-alkylcarbonyl-$C_1$-$C_4$-alkyl, optionally halogen-substituted $C_1$-$C_6$-alkylsulphinyl-$C_1$-$C_6$-alkyl, optionally halogen-substituted $C_1$-$C_6$-alkylsulphonyl-$C_1$-$C_6$-alkyl, optionally halogen-substituted $C_1$-$C_6$-alkoxycarbonyl-$C_1$-$C_6$-alkyl, $C_2$-$C_4$-alkynyloxy, $C_2$-$C_4$-alkynyloxycarbonyl, optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, $C_1$-$C_6$-alkoxycarbonyl-, $C_1$-$C_6$-haloalkoxycarbonyl- or hetaryl-substituted (where hetaryl is itself optionally substituted by $C_1$-$C_6$-alkyl or halogen) $C_3$-$C_6$-cycloalkyl, optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, $C_1$-$C_6$-alkoxycarbonyl-, $C_1$-$C_6$-haloalkoxycarbonyl- or hetaryl-substituted (where hetaryl is itself optionally substituted by $C_1$-$C_6$-alkyl or halogen) $C_3$-$C_6$-cycloalkylcarbonyl, optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, $C_1$-$C_6$-alkoxycarbonyl-, $C_1$-$C_6$-haloalkoxycarbonyl- or hetaryl-substituted (where hetaryl is itself optionally substituted by $C_1$-$C_6$-alkyl or halogen) $C_3$-$C_6$-cycloalkyl-$C_1$-$C_6$-alkyl, optionally halogen-, cyano- (including in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_1$-$C_6$-alkyl-$C_3$-$C_6$-cycloalkyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted heterocyclyl-$C_1$-$C_6$-alkyl, optionally halogen-, cyano-, $C_1$-$C_6$-alkyl-, $C_1$-$C_6$-haloalkyl-, $C_1$-$C_6$-alkoxy- or $C_1$-$C_6$-haloalkoxy-substituted aryl-$C_1$-$C_6$-alkyl, optionally halogen-, cyano- (including in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_1$-$C_6$-alkyl-$C_3$-$C_6$-cycloalkyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted hetaryl-$C_1$-$C_6$-alkyl, or $NR^4R^5$ in which $R^4$ and $R^5$ are each independently a radical from the group of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxycarbonyl, or $R^2$ and $R^3$ together with the nitrogen atom to which they are bonded form an optionally $C_1$-$C_6$-alkyl- or $C_1$-$C_6$-alkoxy-substituted 3- to 7-membered ring which optionally contains one or two further heteroatoms from the group of oxygen, nitrogen and sulphur.

Particularly preferred substituents and ranges of the radicals listed in the aforementioned compounds (Ia), (Ib) and (Ic) are illustrated hereinafter.

$R^1$ is hydrogen or methyl.

$R^2$ is hydrogen, $C_1$-$C_4$-alkyl, $C_1$-$C_4$-haloalkyl, $C_1$-$C_4$-alkoxy, $C_2$-$C_3$-alkenyl, $C_1$-$C_2$-alkoxy-$C_1$-$C_2$-alkyl, $C_1$-$C_2$-alkylcarbonyl, $C_1$-$C_2$-alkoxycarbonyl or in each case optionally halogen-substituted cyclopropylcarbonyl, cyclopentylcarbonyl or cyclohexylcarbonyl.

$R^3$ is hydrogen, $C_1$-$C_4$-alkyl, $C_1$-$C_4$-haloalkyl, cyano-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, optionally halogen-substituted $C_1$-$C_2$-alkoxy-$C_1$-$C_4$-alkyl, optionally halogen-substituted bis($C_1$-$C_2$-alkoxy)-$C_1$-$C_4$-alkyl, optionally halogen-substituted $C_1$-$C_4$-alkylthio-$C_1$-$C_4$-alkyl, optionally halogen-substituted $C_1$-$C_4$-alkylcarbonyl-$C_1$-$C_4$-alkyl, optionally halogen-substituted $C_1$-$C_4$-alkylsulphinyl-$C_1$-$C_4$-alkyl, optionally halogen-substituted $C_1$-$C_4$-alkylsulphonyl-$C_1$-$C_4$-alkyl, optionally halogen-substituted $C_1$-$C_4$-alkoxycarbonyl-$C_1$-$C_4$-alkyl, $C_2$-$C_4$-alkynyloxy, $C_2$-$C_4$-alkynyloxycarbonyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkoxycarbonyl-, $C_1$-$C_4$-haloalkoxycarbonyl- or pyridyl-substituted (where pyridyl is itself optionally substituted by $C_1$-$C_4$-alkyl or halogen) $C_3$-$C_6$-cycloalkyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkoxycarbonyl-, $C_1$-$C_4$-haloalkoxycarbonyl- or pyridyl-substituted (where pyridyl is itself optionally substituted by $C_1$-$C_4$-alkyl or halogen) $C_3$-$C_6$-cycloalkylcarbonyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkoxycarbonyl-, $C_1$-$C_4$-haloalkoxycarbonyl- or pyridyl-substituted (where pyridyl is itself optionally substituted by $C_1$-$C_4$-alkyl or halogen) $C_3$-$C_6$-cycloalkyl-$C_1$-$C_4$-alkyl, optionally halogen-, cyano- (including in the alkyl moiety), nitro-, $C_1$-$C_4$-alkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_1$-$C_4$-alkyl-$C_3$-$C_6$-cycloalkyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted heterocyclyl-$C_1$-$C_4$-alkyl, optionally halogen-, cyano-, $C_1$-$C_4$-alkyl-, $C_1$-$C_4$-haloalkyl-, $C_1$-$C_4$-alkoxy- or $C_1$-$C_4$-haloalkoxy-substituted aryl-$C_1$-$C_4$-alkyl, optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_1$-$C_4$-alkyl-$C_3$-$C_6$-cycloalkyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted hetaryl-$C_1$-$C_4$-alkyl or $R^2$ and $R^3$ together with the nitrogen atom to which they are bonded form an optionally $C_1$-$C_4$-alkyl- or $C_1$-$C_4$-alkoxy-substituted 3- to 7-membered ring which optionally contains one or two further heteroatoms from the group of oxygen, nitrogen and sulphur.

Very particularly preferred substituents and ranges of the radicals listed in the aforementioned compounds (Ia), (Ib) and (Ic) are illustrated hereinafter.

$R^1$ is hydrogen or methyl.

$R^2$ is hydrogen, methyl, ethyl, $CH_2CF_3$, $CH_2CF_2CH_3$, $CH_2CHF_2$, $CH_2CF_2CHF_2$, $CH_2CH_2F$, $CH_2$—$CHF$—$CH_3$, $CH_2CF_2Br$, $CH_2CFCl_2$, $CH(CH_3)CH_2F$, $CH_2CCl_3$, $CH_2CClF_2$, $CH_2CH_2CH_2F$, $CH_2CH(CH_3)Cl$, $CHCF_3CH(CH_3)_2$, $CH(CF_3)_2$, $CH_2CH_2Cl$, $CHCF_3CH_2CH_2CH_3$ or $CH_2CF_2CF_3$, methoxy, ethoxy, vinyl, $CH_2OCH_3$, $CH_2OCH_2CH_3$, methylcarbonyl, ethylcarbonyl, methoxycarbonyl, ethoxycarbonyl, cyclopropylcarbonyl or fluorocyclopropylcarbonyl.

$R^3$ is hydrogen, methyl, ethyl, $CH_2CF_3$, $CH_2CF_2CH_3$, $CH_2CHF_2$, $CH_2CF_2CHF_2$, $CH_2CH_2F$, $CH_2$—$CHF$—$CH_3$, $CH_2CF_2Br$, $CH_2CFCl_2$, $CH(CH_3)CH_2F$, $CH_2CCl_3$, $CH_2CClF_2$, $CH_2CH_2CH_2F$, $CH_2CH(CH_3)Cl$, $CHCF_3CH(CH_3)_2$, $CH(CF_3)_2$, $CH_2CH_2Cl$, $CHCF_3CH_2CH_2CH_3$, $CH_2CF_2CF_3$, $C(CH_3)_2CN$, $C(CN)CH(CH_3)_2$, $CH_2CN$, $CH_2CH_2CN$, vinyl, $C(CH_3)_2CCH$, $CH_2CCCH_3$, methoxy, ethoxy, $CH_2CH(CH_3)(OCH_3)$, $CH_2C(CH_3)_2(OCH_3)$, $CH(CH_3)CH(OCH_3)_2$, $CH_2C(CH_3)(OCH_3)_2$, $C(CH_3)_2$—$CH_2SCH_3$, $CH_2CH_2SCH_3$, $CHCH_3CH_2SCH_3$, optionally halogen-substituted $C_1$-$C_4$-alkylcarbonyl-$C_1$-$C_4$-alkyl, $CH_3SO_2CH_2C(CH_3)_2$, $CH_3SO_2CH_2CHCH_3$, propargyloxy, cyanocyclopropyl, fluorocyclopropyl, trifluoromethylcyclopropyl, trifluoromethylcyclohexyl, methoxycarbonylcyclopropyl, fluorocyclopropylcarbonyl, cyclopropylmethyl, cyclohexylmethyl, 1-cyano-1-cyclopropyleth-1-yl, 1,3-dioxolan-2-ylmethyl, 4-methyl-1,3-dioxolan-2-ylmethyl, tetrahydrofurylmethyl, tetrahydropyranylmethyl, 2,2-dimethyl-1,3-dioxolan-5-ylmethyl, 2-methyltetrahydrofur-2-ylmethyl, α-methyl-3,5-dimethyltriazol-1-yl-ethyl, 1,5-dimethyl-1,3-oxazol-4-ylmethyl, optionally halogen-, cyano-, methyl-, ethyl-, methoxy- or ethoxy-substituted benzyl or optionally halogen-, cyano-, methyl-, methoxy- or ethoxy-substituted pyrimidylmethyl, (especially pyrimid-2-ylmethyl, α-methyl-pyrimidylmethyl, 4-bromopyrimid-2-ylmethyl, 2-methylpyrimid-4-ylmethyl, 4,6-dimethylpyrimid-2-ylmethyl, 4-iodopyrimid-2-ylmethyl, 2-ethylpyrimid-6-ylmethyl, 5-chloropyrimid-2-ylmethyl, 5-bromopyrimid-2-ylmethyl, 5-cyanopyrimid-2-ylmethyl, 4,6-dimethoxypyrimid-2-ylmethyl and 4,6-diethoxy-2-pyrimid-2-ylmethyl), oxadiazolylmethyl, oxazolylmethyl, 5-methylpyrazin-2-yl, α-methylpyrid-2-ylmethyl, imidazolylmethyl, 6-chloropyridin-3-ylmethyl, thiazolylmethyl, furanylmethyl, 1,5-dimethylpyrazol-3-ylmethyl, 3-cyclopropyl-1,2,4-oxadiazol-5-ylmethyl, 6-bromopyrid-2-ylmethyl, or $R^2$ and $R^3$ together with the nitrogen atom to which they are bonded form an optionally $C_1$-$C_4$-alkyl- or $C_1$-$C_4$-alkoxy-substituted 3- to 7-membered ring which optionally contains one or two further heteroatoms from the group of oxygen, nitrogen and sulphur; for example, $R^2$ and $R^3$ together are $CH_2CH_2CH_2$ or $CH_2CH_2CH_2O$.

Preferred substituents and ranges of the radicals listed in the abovementioned compounds (Id) are illustrated hereinafter.

$R^1$ is hydrogen or $C_1$-$C_6$-alkyl and here in turn preferably hydrogen or methyl.

$R^2$ is hydrogen, $C_1$-$C_6$-alkyl, $C_1$-$C_6$-haloalkyl, $C_1$-$C_4$-alkoxy, $C_1$-$C_4$-haloalkoxy, $C_2$-$C_4$-alkenyl, $C_1$-$C_4$-alkoxy-$C_1$-$C_4$-alkyl, optionally halogen-substituted $C_1$-$C_4$-alkylcarbonyl, optionally halogen-substituted $C_1$-$C_4$-alkoxycarbonyl or optionally halogen-substituted $C_3$-$C_6$-cycloalkylcarbonyl.

$R^3$ is $C_1$-$C_6$-haloalkyl, cyano-$C_1$-$C_6$-alkyl, $C_2$-$C_4$-haloalkenyl, $C_2$-$C_4$-haloalkynyl, $C_1$-$C_6$-alkoxy, $C_1$-$C_6$-haloalkoxy, optionally halogen-substituted $C_1$-$C_6$-alkoxy-$C_1$-$C_6$-alkyl, optionally halogen-substituted bis($C_1$-$C_6$-alkoxy)-$C_1$-$C_6$-alkyl, optionally halogen-substituted $C_1$-$C_6$-alkylthio-$C_1$-$C_6$-alkyl, optionally halogen-substituted $C_1$-$C_4$-alkylcarbonyl-$C_1$-$C_4$-alkyl, optionally halogen-substituted $C_1$-$C_6$-alkylsulphinyl-$C_1$-$C_6$-alkyl, optionally halogen-substituted $C_1$-$C_6$-alkylsulphonyl-$C_1$-$C_6$-alkyl, optionally halogen-substituted $C_1$-$C_6$-alkoxycarbonyl-$C_1$-$C_6$-alkyl, $C_2$-$C_4$-alkynyloxy, $C_2$-$C_4$-alkynyloxycarbonyl, halogen-, cyano-, $C_1$-$C_6$-alkyl-, $C_1$-$C_6$-haloalkyl-, $C_1$-$C_6$-alkoxy-, $C_1$-$C_6$-haloalkoxy-, $C_1$-$C_6$-alkoxycarbonyl-, $C_1$-$C_6$-haloalkoxycarbonyl- or hetaryl-substituted (where hetaryl is itself optionally substituted by $C_1$-$C_6$-alkyl or halogen) $C_3$-$C_6$-cycloalkyl, optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, $C_1$-$C_6$-alkoxycarbonyl-, $C_1$-$C_6$-haloalkoxycarbonyl- or hetaryl-substituted (where hetaryl is itself optionally substituted by $C_1$-$C_6$-alkyl or halogen) $C_3$-$C_6$-cycloalkylcarbonyl, optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, $C_1$-$C_6$-alkoxycarbonyl-, $C_1$-$C_6$-haloalkoxycarbonyl- or hetaryl-substituted (where hetaryl is itself optionally substituted by $C_1$-$C_6$-alkyl or halogen) $C_3$-$C_6$-cycloalkyl-$C_1$-$C_6$-alkyl, optionally halogen-, cyano- (including in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkyl-$C_3$-$C_6$-cycloalkyl-, $C_1$-$C_6$-alkylcarbonyl-, $C_1$-$C_6$-alkoxycarbonyl- or aminocarbonyl-substituted heterocyclyl-$C_1$-$C_6$-alkyl, halogen-, cyano-, $C_1$-$C_6$-alkyl-, $C_1$-$C_6$-haloalkyl-, $C_1$-$C_6$-alkoxy- or $C_1$-$C_6$-haloalkoxy-substituted aryl-$C_1$-$C_6$-alkyl, or optionally halogen-, cyano- (including in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkyl-$C_3$-$C_6$-cycloalkyl-, $C_1$-$C_6$-alkylcarbonyl-, $C_1$-$C_6$-alkoxycarbonyl- or aminocarbonyl-substituted hetaryl-$C_1$-$C_6$-alkyl.

Particularly preferred substituents and ranges of the radicals listed in the abovementioned compounds (Id) are illustrated hereinafter.

$R^1$ is hydrogen or methyl.

$R^2$ is hydrogen, $C_1$-$C_4$-alkyl, $C_1$-$C_4$-haloalkyl, $C_1$-$C_4$-alkoxy, $C_2$-$C_3$-alkenyl, $C_1$-$C_2$-alkoxy-$C_1$-$C_2$-alkyl, $C_1$-$C_2$-alkylcarbonyl, $C_1$-$C_2$-alkoxycarbonyl or in each case optionally halogen-substituted cyclopropylcarbonyl, cyclopentylcarbonyl or cyclohexylcarbonyl.

$R^3$ is $C_1$-$C_4$-haloalkyl, cyano-$C_1$-$C_4$-alkyl, $C_2$-$C_4$-haloalkenyl, $C_2$-$C_4$-haloalkynyl, $C_1$-$C_4$-alkoxy, $C_1$-$C_4$-haloalkoxy, optionally halogen-substituted $C_1$-$C_2$-alkoxy-$C_1$-$C_4$-alkyl, optionally halogen-substituted bis($C_1$-$C_2$-alkoxy)-$C_1$-$C_4$-alkyl, optionally halogen-substituted $C_1$-$C_4$-alkylthio-$C_1$-$C_4$-alkyl, optionally halogen-substituted $C_1$-$C_4$-alkylcarbonyl-$C_1$-$C_4$-alkyl, optionally halogen-substituted $C_1$-$C_4$-alkylsulphinyl-$C_1$-$C_4$-alkyl, optionally halogen-substituted $C_1$-$C_4$-alkylsulphonyl-$C_1$-$C_4$-alkyl, optionally halogen-substituted $C_1$-$C_4$-alkoxycarbonyl-$C_1$-$C_4$-alkyl, $C_2$-$C_4$-alkynyloxy, $C_2$-$C_4$-alkynyloxycarbonyl, halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkoxycarbonyl-, $C_1$-$C_4$-haloalkoxycarbonyl- or pyridyl-substituted (where pyridyl is itself optionally substituted by $C_1$-$C_4$-alkyl or halogen) $C_3$-$C_6$-cycloalkyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkoxycarbonyl-, $C_1$-$C_4$-haloalkoxycarbonyl- or pyridyl-substituted (where pyridyl is itself optionally substituted by $C_1$-$C_4$-alkyl or halogen) $C_3$-$C_6$-cycloalkylcarbonyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkoxycarbonyl-, $C_1$-$C_4$-haloalkoxycarbonyl- or pyridyl-substituted (where pyridyl is itself optionally substituted by $C_1$-$C_4$-alkyl or halogen) $C_3$-$C_6$-cycloalkyl-$C_1$-$C_4$-alkyl, optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkyl-$C_3$-$C_6$-cycloalkyl-, $C_1$-$C_4$-alkylcarbonyl-, $C_1$-$C_4$-alkoxycarbonyl- or aminocarbonyl-substituted heterocyclyl-$C_1$-$C_4$-alkyl, halogen-, cyano-, $C_1$-$C_4$-haloalkyl-, $C_1$-$C_4$-alkoxy- or $C_1$-$C_4$-haloalkoxy-substituted aryl-$C_1$-$C_4$-alkyl or optionally halogen-, cyano- (including in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkyl-$C_3$-$C_6$-cycloalkyl-, $C_1$-$C_4$-alkylcarbonyl-, $C_1$-$C_4$-alkoxycarbonyl- or aminocarbonyl-substituted hetaryl-$C_1$-$C_4$-alkyl.

Very particularly preferred substituents and ranges of the radicals listed in the abovementioned compounds (Id) are illustrated hereinafter.

$R^1$ is hydrogen or methyl.

$R^2$ is hydrogen, methyl, ethyl, $CH_2CF_3$, $CH_2CF_2CH_3$, $CH_2CHF_2$, $CH_2CF_2CHF_2$, $CH_2CH_2F$, $CH_2$—$CHF$—$CH_3$, $CH_2CF_2Br$, $CH_2CFCl_2$, $CH(CH_3)CH_2F$, $CH_2CCl_3$, $CH_2CClF_2$, $CH_2CH_2CH_2F$, $CH_2CH(CH_3)Cl$, $CHCF_3CH(CH_3)_2$, $CH(CF_3)_2$, $CH_2CH_2Cl$, $CHCF_3CH_2CH_2CH_3$ or $CH_2CF_2CF_3$, methoxy, ethoxy, vinyl, $CH_2OCH_3$, $CH_2OCH_2CH_3$, methylcarbonyl, ethylcarbonyl, methoxycarbonyl, ethoxycarbonyl, cyclopropylcarbonyl or fluorocyclopropylcarbonyl.

$R^3$ is $CH_2CF_3$, $CH_2CF_2CH_3$, $CH_2CHF_2$, $CH_2CF_2CHF_2$, $CH_2CH_2F$, $CH_2$—$CHF$—$CH_3$, $CH_2CF_2Br$, $CH_2CFCl_2$, $CH(CH_3)CH_2F$, $CH_2CCl_3$, $CH_2CClF_2$, $CH_2CH_2CH_2F$, $CH_2CH(CH_3)Cl$, $CHCF_3CH(CH_3)_2$, $CH(CF_3)_2$, $CH_2CH_2Cl$, $CHCF_3CH_2CH_2CH_3$, $CH_2CF_2CF_3$, $C(CH_3)_2CN$, $C(CN)CH(CH_3)_2$, $CH_2CN$, $CH_2CH_2CN$, methoxy, ethoxy, $CH_2CH(CH_3)(OCH_3)$, $CH_2C(CH_3)_2(OCH_3)$, $CH(CH_3)CH(OCH_3)_2$, $CH_2C(CH_3)(OCH_3)_2$, $C(CH_3)_2$—$CH_2SCH_3$, $CH_2CH_2SCH_3$, $CHCH_3CH_2SCH_3$, optionally halogen-substituted $C_1$-$C_4$-alkylcarbonyl-$C_1$-$C_4$-alkyl, $CH_3SO_2CH_2C(CH_3)_2$, $CH_3SO_2CH_2CHCH_3$, propargyloxy, cyanocyclopropyl, fluorocyclopropyl, trifluoromethylcyclopropyl, trifluoromethylcyclohexyl, methoxycarbonylcyclopropyl, fluorocyclopropylcarbonyl, cyclopropylmethyl, cyclohexylmethyl, 1-cyano-1-cyclopropyleth-1-yl, 1,3-dioxolan-2-ylmethyl, 4-methyl-1,3-dioxolan-2-ylmethyl, tetrahydrofurylmethyl, tetrahydropyranylmethyl, 2,2-dimethyl-1,3-dioxolan-5-ylmethyl, 2-methyltetrahydrofur-2-ylmethyl, α-methyl-3,5-dimethyltriazol-1-yl-ethyl, 1,5-dimethyl-1,3-oxazol-4-ylmethyl, optionally halogen-, cyano-, methyl-, ethyl-, methoxy- or ethoxy-substituted benzyl, or optionally halogen-, cyano-, methyl-, methoxy- or ethoxy-substituted pyrimidylmethyl (especially pyrimid-2-ylmethyl, α-methyl-pyrimidylmethyl, 4-bromopyrimid-2-ylmethyl, 2-methylpyrimid-4-ylmethyl, 4,6-dimethylpyrimid-2-ylmethyl, 4-iodopyrimid-2-ylmethyl, 2-ethylpyrimid-6-ylmethyl, 5-chloropyrimid-2-ylmethyl, 5-bromopyrimid-2-ylmethyl, 5-cyanopyrimid-2-ylmethyl, 4,6-dimethoxypyrimid-2-ylmethyl and 4,6-diethoxy-2-pyrimid-2-ylmethyl), oxadiazolylmethyl, oxazolylmethyl, 5-methylpyrazin-2-yl, α-methylpyrid-2-ylmethyl, imidazolylmethyl, 6-chloropyridin-3-ylmethyl, thiazolylmethyl, furanylmethyl, 1,5-dimethylpyrazol-3-ylmethyl, 3-cyclopropyl-1,2,4-oxadiazol-5-ylmethyl, 6-bromopyrid-2-ylmethyl.

Preferred substituents and ranges of the radicals listed in the abovementioned compounds (Ie) are illustrated hereinafter.

$R^2$ is hydrogen or $C_1$-$C_6$-alkyl.

$R^3$ is hydrogen or $C_1$-$C_6$-alkyl.

Particularly preferred substituents and ranges of the radicals listed in the abovementioned compounds (Ie) are illustrated hereinafter.

$R^2$ is hydrogen or $C_1$-$C_4$-alkyl.

$R^3$ is hydrogen or $C_1$-$C_4$-alkyl.

Very particularly preferred substituents and ranges of the radicals listed in the abovementioned compounds (Ie) are illustrated hereinafter.

$R^2$ is hydrogen, methyl, ethyl, n-propyl or i-propyl.

$R^3$ is hydrogen, methyl, ethyl, n-propyl or i-propyl.

In the preferred definitions, unless stated otherwise, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl and is in turn preferably phenyl, hetaryl (including as part of a larger unit, for example hetarylalkyl) is selected from the group of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, heterocyclyl (including as part of a larger unit, for example heterocyclylalkyl) is selected from the group of 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,3-dihydrothien-2-yl, 2,3-dihydrothien-3-yl, 2,4-dihydrothien-2-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl.

In the particularly preferred definitions, unless stated otherwise, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl and is in turn preferably phenyl, hetaryl (including as part of a larger unit, for example hetarylalkyl) is selected from the group of pyrimidyl, oxadiazolyl, oxazolyl, pyrazinyl, imidazolyl, thiazolyl and furanyl, heterocyclyl (including as part of a larger unit, for example heterocyclylalkyl) is selected from the group of 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5 isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,3-dihydrothien-2-yl, 2,3-dihydrothien-3-yl, 2,4-dihydrothien-2-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl.

Halogen-substituted radicals, e.g. haloalkyl, are mono- or polyhalogenated up to the maximum possible number of substituents. In the case of polyhalogenation, the halogen atoms may be the same or different. Halogen represents fluorine, chlorine, bromine or iodine, especially fluorine, chlorine or bromine.

Preference, particular preference or very particular preference is given to compounds which in each case bear the substituents specified under preferred, particularly preferred or very particularly preferred.

Saturated or unsaturated hydrocarbon radicals such as alkyl or alkenyl may, also in conjunction with heteroatoms, as, for example, in alkoxy, as far as possible, in each case be straight-chain or branched.

Optionally substituted radicals may be mono- or polysubstituted, where the substituents may be the same or different in the case of polysubstitutions.

The radical definitions and illustrations listed above, in general or within preferred ranges, apply correspondingly to the end products and to the starting materials and intermediates. These radical definitions can be combined with one another as desired, i.e. including between the individual preferred ranges.

Preference is given in accordance with the invention to compounds of the formula (I) in which a combination of the definitions listed above as preferred is present.

Particular preference is given in accordance with the invention to compounds of the formula (I) in which a combination of the definitions listed above as particularly preferred is present.

Very particular preference is given in accordance with the invention to compounds of the formula (I) in which a combination of the definitions listed above as very particularly preferred is present.

An emphasized group of inventive compounds is that of the compounds defined under (Ia).

A further emphasized group of inventive compounds is that of the compounds defined under (Ib)

A further emphasized group of inventive compounds is that of the compounds defined under (Ic)

A further emphasized group of inventive compounds is that of the compounds defined under (Id)

A further emphasized group of inventive compounds is that of the compounds defined under (Ie)

In a further emphasized group of inventive compounds, $R^3$ is haloalkyl.

In a further emphasized group of inventive compounds, $R^3$ is heterocyclylalkyl.

In a further emphasized group of inventive compounds, $R^3$ is hetarylalkyl.

In a further emphasized group of inventive compounds, X is oxygen.

In a further emphasized group of inventive compounds, X is sulphur.

The preparation of inventive compounds of the formula (I) in which $G^2$ is the (A) radical, and of corresponding precursors, is illustrated in the following reaction schemes.

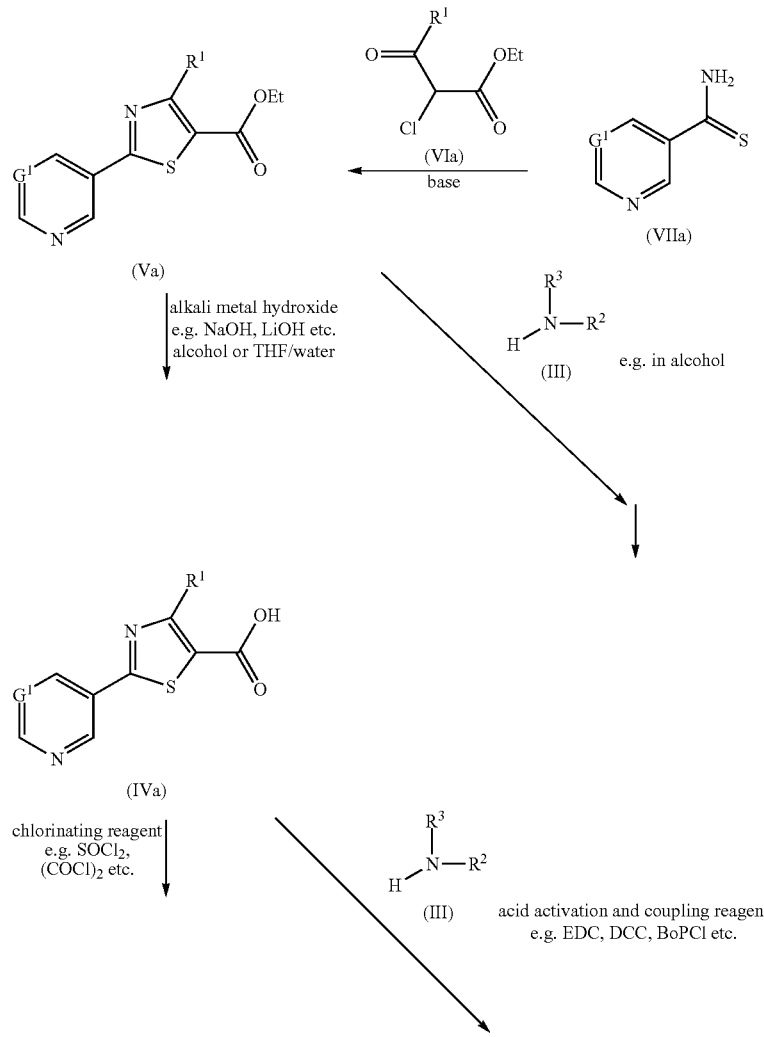

Reaction Scheme 1

-continued

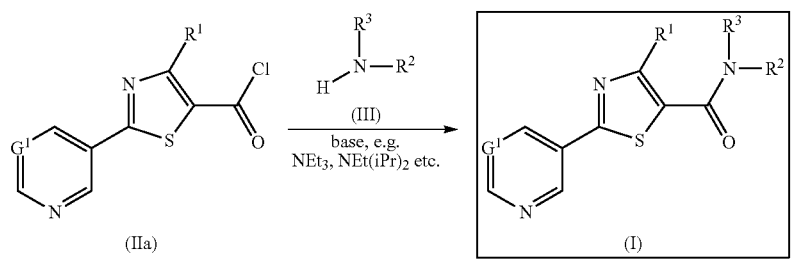

The compounds of the formula (VIIa) in which $G^1$ is as defined above, which are required as starting materials, are known or obtainable by known methods, for example as described in Synthetic Communications 35, 5, 2005, 761. Compounds of the formula (Va) in which $R^1$ is alkyl are preparable using the standard methods specified in Reaction Scheme 1; cf. DE 2221647. Reaction of a thioamide (VIIa) with the ester of the formula (VIa) in the presence of a base, for example triethylamine, affords the thiazole (Va). The compounds of the formula (Va) in which $R^1$ is hydrogen are preparable in analogy to the methods described in Helvetica Chimica Acta 1944, 1432-1436. The chloroformyl ester used there can be prepared as described in Chemische Berichte, 1910, 3528-3533. Preferably, however, the sodium salt, prepared in analogy to the potassium salt described there, of the chloroformyl ester is used directly for the reaction with a thioamide of the formula (VIIa) without addition of a base; see Example 3.

The thiazole of the formula (Va) can be converted using the standard methods specified in Reaction Scheme 1 (cf. DE 2221647), first to the acid of the formula (IVa) and then to the acid chloride of the formula (IIa). Further reaction with the amine of the formula (III) in which $R^2$ and $R^3$ are each as defined above, in a diluent, for example dichloromethane or tetrahydrofuran and in the presence of a base, for example triethylamine or diisopropylethylamine, leads to inventive compounds of the formula (I) in which X is oxygen.

The compounds of the formula (I) can be prepared directly from the acids of the formula (IVa) by reaction with amines of the formula (III) in the presence of coupling agents, for example EDC (1-ethyl-3-[3-dimethylaminopropyl]carbodiimide hydrochloride), DCC (dicyclohexylcarbodiimide) or BoPCl (bis(2-oxo-3-oxazolidinyl)phosphinic chloride).

The compounds of the formula (I) can also be prepared directly from the esters of the formula (VIa) by reaction with amines of the formula (III) in a diluent, for example ethanol, while heating.

Compounds of the formula (I) in which $R^2$ is hydrogen or $R^3$ is hydrogen can be derivatized by alkylation, for example by reaction with an alkylating agent such as methyl iodide in a diluent such as DMF using a base (e.g. sodium hydride).

The amines of the formula (III) are known or can be prepared by methods known in principle, for example by reduction of amides, as described in EP 0 030 092, page 86; see also Preparation Example 1.

Alternatively, compounds of the formula (I) can also be prepared by Suzuki coupling according to Reaction Scheme 2. This involves converting the acid of the formula (Xa) (cf., for example, Helvetica Chim Acta 27, 1432 (1944) and J. Het. Chem. 22(6) 1621 (1985)), either directly or after conversion to the acid chloride of the formula (XIa), to the amide of the formula (IXa) and then coupling the latter with the boric ester of the formula (VIIIa) to give inventive compounds of the formula (I) (cf., for example, J. Med. Chem 48 (1), 224 (2005)). The boron compounds of the formula (VIIIa) are known or obtainable by known methods (see, for example, Tetrahedron 57 (49), 9813 (2001), Journal of Organic. Chemistry 70 (15), 6034 (2005), and also Tetrahedron Letters 43, (2002), 4285-4287 and Journal of Organic Chemistry 2002, 67, 5394-5397).

Reaction Scheme 2

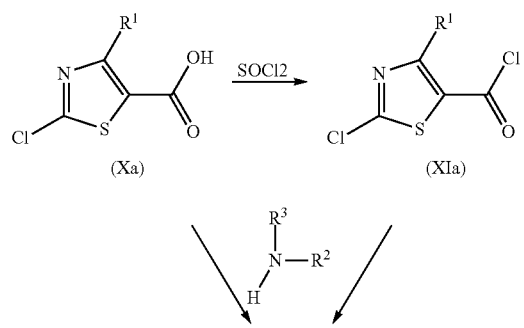

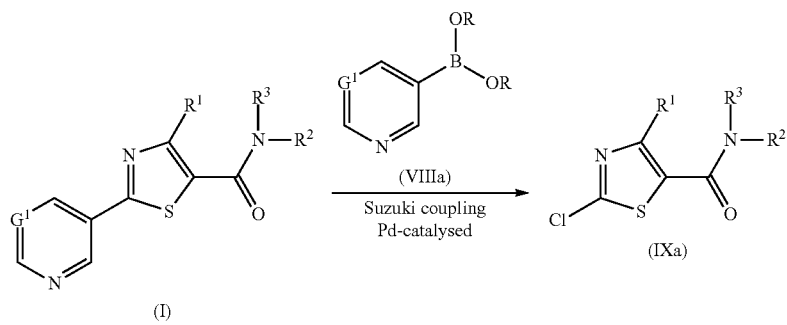

Compounds of the formula (I) in which X is sulphur can be prepared from the compounds of the formula (I) in which X is oxygen by reaction with a sulphurizing reagent, for example Lawesson's reagent or $P_4S_{10}$. N-Oxides can be obtained, for example, by reacting compounds of the formula (I) with mCPBA (meta-chloroperbenzoic acid). Salts of compounds of the formula (I) are obtainable according to Reaction Scheme 3 (shown there by way of example for the (A) radical), by reacting compounds of the formula (I) with compounds of the formula RX in which, for example, X is halogen such as chlorine or bromine and R is an optionally substituted alkyl, alkenyl or alkynyl radical (Reaction Scheme 3).

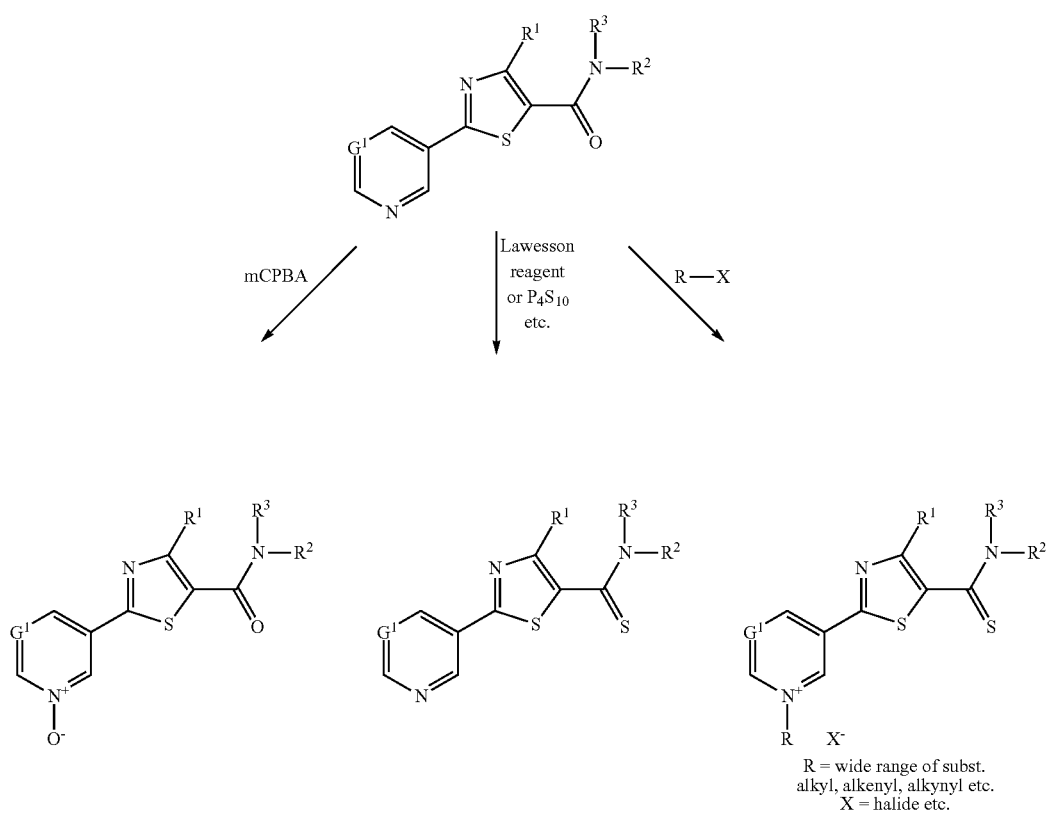

The preparation of inventive compounds of the formula (I) in which $G^2$ is the (B) radical and corresponding precursors is explained in the reaction schemes which follow.

The reaction sequence proceeding from the ester of the formula (Vb) corresponds to that in Reaction Scheme 1, proceeding there from the ester of the formula (Va), and the statements made there apply correspondingly (Reaction Scheme 4).

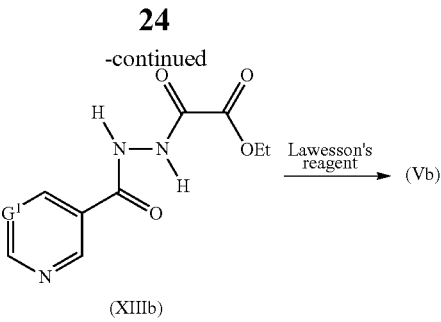

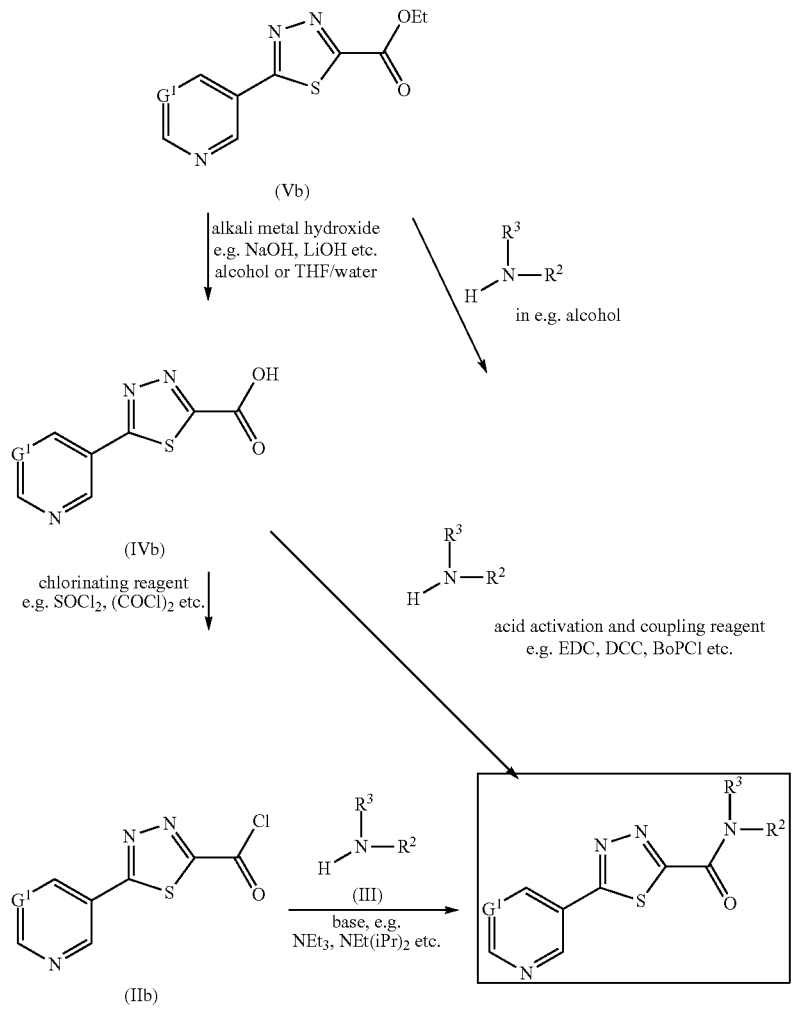

The esters of the formula (Vb) are novel; they can be prepared by processes known in principle, for example in analogy to Liquid Crystals Today, Vol 14, 1, 2005, 15-18, for example as shown in Reaction Scheme 5.

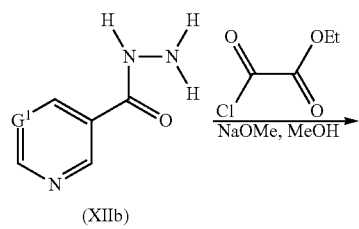

The hydrazide of the formula (XIIb) is reacted in the presence of a base, for example triethylamine or sodium methoxide, in a diluent, for example dimethylformamide (DMF) or methanol, with ethyl oxalyl chloride to give the diacylhydrazine compound of the formula (XIIIb), which then reacts in a coupling agent, for example with Lawesson's reagent, to give the thiadiazole of the formula (Vb). Hydrazides of the formula (XIIb) are described, for example, in Journal of Medicinal Chemistry, 32, 3, 1989, 583-593 and are obtainable by hydrazinolysis of the corresponding carboxylic esters. Novel, and part of the subject-matter of the invention, are also the compounds of the formulae (IIb), (IVb) and (Vb).

The preparation of inventive compounds of the formula (I) in which G² is the (C) radical and of corresponding precursors is illustrated in the Reaction Schemes which follow.

The reaction sequence proceeding from the ester of the formula (Vc) corresponds to that in Reaction Scheme 1, proceeding there from the ester of the formula (Va), and the statements made there apply in turn (Reaction Scheme 6).

Reaction Scheme 7

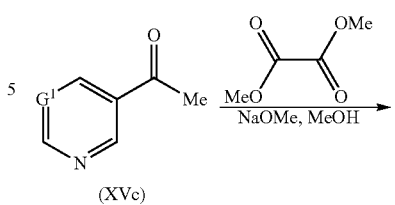

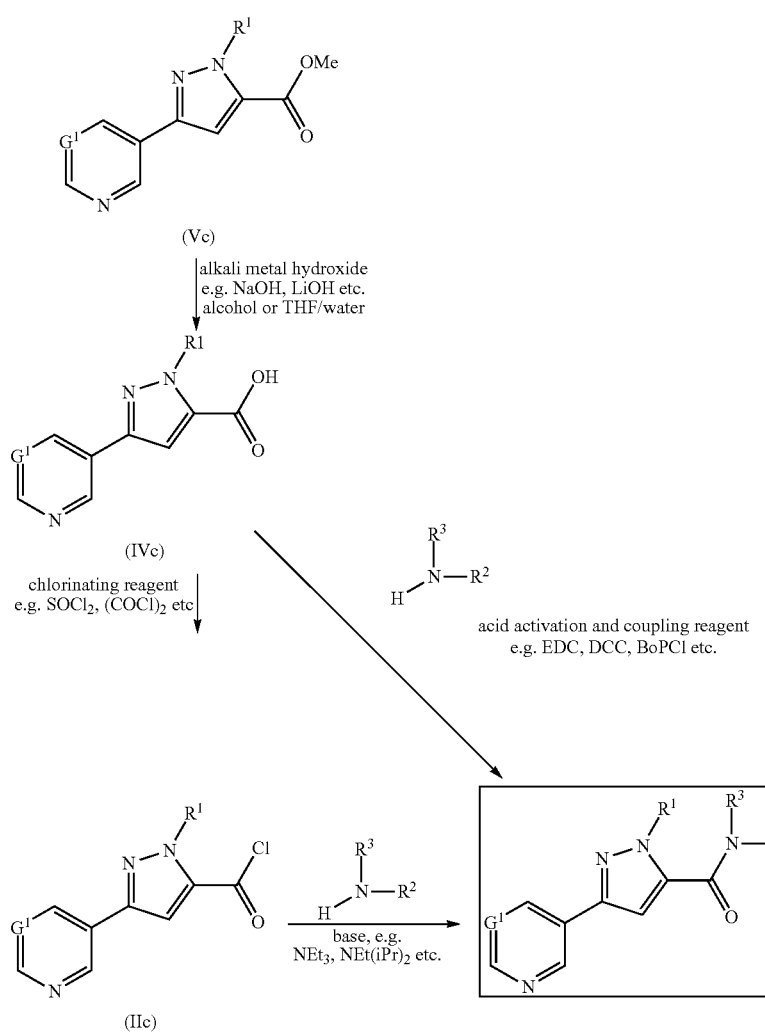

Compounds of the formulae (IVc) and (Vc) in which R¹ is hydrogen are known (cf. WO 2005/090328; WO 1999/62885; Bioorganic & Medicinal Chemistry Letters (2000), 10 (11), 1211-1214; J. Chem. Soc. (1933), 350). Compounds of the formulae (IVc) and (Vc) in which R¹ is alkyl, especially methyl, are novel and also form part of the subject-matter of the invention.

The preparation of the ester of the formula (Vc) is shown in Reaction Scheme 7.

-continued

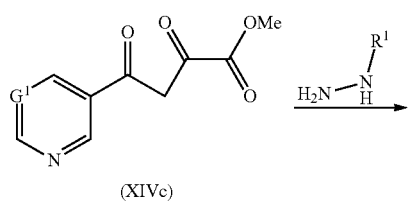

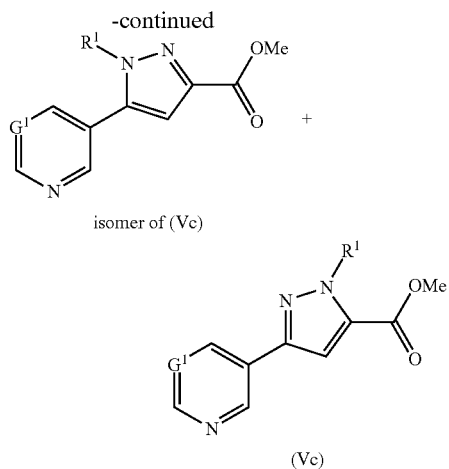

isomer of (Vc)

(Vc)

First, the diketo ester of the formula (XVIc) is prepared, by reacting the methyl ketone of the formula (XVc) with the oxalic ester in the presence of sodium methoxide in methanol (see also WO 2004/002409 and WO 2004/016741). Subsequent reaction with the hydrazine derivative of the formula $H_2NNHR^1$ in an alcohol, e.g. methanol, as a diluent leads to the ester of the formula (Vc) and to the isomer of (Vc) shown above. The two isomers can, for example, be separated by chromatography. The compounds of the formula (XVc) are known or can be obtained by known processes (cf., for example, EP334146, EP1270535, Monatshefte für Chemie 126(6/7), 805 (1995), JOC 66(12), 4340 (2001)).

Compounds of the formula (I) in which X is oxygen can be converted with a sulphurizing reagent to compounds of the formula (I) in which X is sulphur.

The sulphidating agents (sulphurizing reagents) used are preferably phosphorus reagents, for example diphosphorus pentasulphide ($P_2S_5$), diphosphorus pentasulphide/pyridine ($P_2S_5$/Py), diphosphorus pentasulphide/triethylamine ($P_2S_5$/$NEt_3$), diphosphorus pentasulphide/sodium hydrogencarbonate ($P_2S_5$/$NaHCO_3$ "Scheeren's reagent") or, more preferably, 2,4-bis(4-methoxyphenyl)-2,4-dithioxo-1,3,2,4-dithiadiphosphetane "Lawesson's reagent (LR)", 2,4-bis(4-phenoxyphenyl)-2,4-dithioxo-1,3,2,4-dithiadiphosphetane "Belleau's reagent (BR)" or 2,4-bis(4-phenylthiophenyl)-2,4-dithioxo-1,3,2,4-dithiadiphosphetane.

The compounds of the formula (I) may, if appropriate, be present in different polymorphic forms or as a mixture of different polymorphic forms. Both the pure polymorphs and the polymorph mixtures form part of the subject-matter of the invention and can be used in accordance with the invention.

The inventive active ingredients, in combination with good plant tolerance and favourable toxicity to warm-blooded animals and being tolerated well by the environment, are suitable for protecting plants and plant organs, for increasing harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echi-*

*nococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is furthermore possible to control protozoa, such as *Eimeria.*

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Cameocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyrifoimis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Monomorium pharaonic, Vespa* spp.

From the order of the Isopoda, for example, *Armadillidium vulgare, Oniscus asellus, Porcellio scaber.*

From the order of the Isoptera, for example, *Reticulitermes* spp., *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella immaculata.*

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

The inventive compounds can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). They can also be employed as intermediates or precursors for the synthesis of other active ingredients.

The active ingredients can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active ingredient, synthetic materials impregnated with active ingredient, fertilizers and microencapsulations in polymeric substances.

These formulations are produced in a known manner, for example by mixing the active ingredients with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:
for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE- and/or -POP-ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose, natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active ingredient, preferably between 0.5 and 90%.

The inventive active ingredient can be used in its commercially available formulations and in the use forms, prepared from these formulations, as a mixture with other active ingredients, such as insecticides, attractants, sterilizing agents, bactericides, acaricides, nematicides, fungicides, growth-regulating substances, herbicides, safeners, fertilizers or semiochemicals.

A mixture with other known active ingredients, such as herbicides, fertilizers, growth regulators, safeners, semiochemicals, or else with agents for improving the plant properties, is also possible.

When used as insecticides, the inventive active ingredients can furthermore be present in their commercially available formulations and in the use forms, prepared from these formulations, as a mixture with synergists. Synergists are compounds which increase the action of the active ingredients, without it being necessary for the synergistic agent added to be active itself.

When used as insecticides, the inventive active ingredients can furthermore be present in their commercially available formulations and in the use forms, prepared from these formulations, as mixtures with inhibitors which reduce degradation of the active ingredient after use in the environment of the plant, on the surface of parts of plants or in plant tissues.

The active ingredient content of the use forms prepared from the commercially available formulations can vary within wide limits. The active ingredient concentration of the use forms can be from 0.00000001 to 95% by weight of active ingredient, preferably between 0.00001 and 1% by weight.

The compounds are employed in a customary manner appropriate for the use forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes.

The plant parts also include harvested material, and vegetative and generative propagation material, for example cuttings, tubers, rhizomes, offshoots and seeds.

Inventive treatment of the plants and plant parts with the active ingredients is carried out directly or by allowing the compounds to act on the surroundings, habitat or storage space by the customary treatment methods, for example by immersion, spraying, evaporation, fogging, scattering, painting on, injecting and, in the case of propagation material, in particular in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated in accordance with the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment in accordance with the invention may also result in superadditive ("synergistic") effects. Thus, for example, reduced application rates and/or a widening of the activity spectrum and/or an increase in the activity of the substances and compositions which can be used in accordance with the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated in accordance with the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defense of the plants against animal and microbial pests, such as against insects, mites, phytopathogenic fungi, bacteria and/or viruses, and also increased tolerance of the plants to certain herbicidally active ingredients. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defense of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defense of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active ingredients, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated in accordance with the invention in a particularly advantageous manner with the compounds of the general formula (I) and/or the inventive active ingredient mixtures. The preferred ranges stated above for the active ingredients or mixtures also apply to the treatment of these plants. Particular emphasis is given to the treatment of plants with the compounds or mixtures specifically mentioned in the present text.

The inventive active ingredients act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp.,

*Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp. (*Ctenocephalides canis*, *Ctenocephalides felis*), *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis*, *Periplaneta americana*, *Blattela germanica*, *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The inventive active ingredients of the formula (I) are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the inventive active ingredients.

The inventive active ingredients are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injections (intramuscular, subcutaneous, intravenous, intraperitoneal and the like), implants, by nasal application, by dermal use in the form, for example, of dipping or bathing, spraying, pouring on and spotting on, washing and powdering, and also with the aid of moulded articles containing the active ingredient, such as collars, ear marks, tail marks, limb bands, halters, marking devices and the like.

When used for cattle, poultry, pets and the like, the active ingredients of the formula (I) can be used as formulations (for example powders, emulsions, free-flowing compositions), which comprise the active ingredients in an amount of from 1 to 80% by weight, directly or after 100 to 10 000-fold dilution, or they can be used as a chemical bath.

It has furthermore been found that the inventive compounds also have a strong insecticidal action against insects which destroy industrial materials.

The following insects may be mentioned as examples and as preferred—but without any limitation:

beetles, such as *Hylotrupes bajulus*, *Chlorophorus pilosis*, *Anobium punctatum*, *Xestobium rufovillosum*, *Ptilinus pecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthes rugicollis*, *Xyleborus* spec. *Tryptodendron* spec. *Apate monachus*, *Bostrychus capucins*, *Heterobostrychus brunneus*, *Sinoxylon* spec. *Dinoderus minutus*;

hymenopterons, such as *Sirex juvencus*, *Urocerus gigas*, *Urocerus gigas taignus*, *Urocerus augur*;

termites, such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis*, *Coptotermes formosanus*;

bristletails, such as *Lepisma saccharina*.

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The inventive compounds can likewise be employed for protecting objects which come into contact with saltwater or brackish water, in particular hulls, screens, nets, buildings, moorings and signalling systems, against fouling.

Furthermore, the inventive compounds, alone or in combinations with other active ingredients, may be employed as antifouling agents.

In domestic, hygiene and stored-product protection, the active ingredients are also suitable for controlling animal pests, in particular insects, arachnids and mites, which are found in enclosed spaces such as, for example, dwellings, factory halls, offices, vehicle cabins and the like. They can be employed alone or in combination with other active ingredients and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus*, *Argas reflexus*, *Bryobia* ssp., *Dermanyssus gallinae*, *Glyciphagus domesticus*, *Ornithodorus moubat*, *Rhipicephalus sanguineus*, *Trombicula alfreddugesi*, *Neutrombicula autumnalis*, *Dermatophagoides pteronissimus*, *Dermatophagoides forinae*.

From the order of the Araneae, for example, *Avicularii-dae*, *Araneidae*.

From the order of the Opiliones, for example, *Pseudoscorpiones chelifer*, *Pseudoscorpiones cheiridium*, *Opiliones phalangium*.

From the order of the Isopoda, for example, *Oniscus asellus*, *Porcellio scaber*.

From the order of the Diplopoda, for example, *Blaniulus guttulatus*, *Polydesmus* spp.

From the order of the Chilopoda, for example, *Geophilus* spp.

From the order of the Zygentoma, for example, *Ctenolepisma* spp., *Lepisma saccharina*, *Lepismodes inquilinus*.

From the order of the Blattaria, for example, *Blatta orientalies*, *Blattella germanica*, *Blattella asahinai*, *Leucophaea maderae*, *Panchlora* spp., *Parcoblatta* spp., *Periplaneta australasiae*, *Periplaneta americana*, *Periplaneta brunnea*, *Periplaneta fuliginosa*, *Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae*, *Necrobia* spp., *Ptinus* spp., *Rhizopertha dominica*, *Sitophilus granarius*, *Sitophilus oryzae*, *Sitophilus zeamais*, *Stegobium paniceum*.

From the order of the Diptera, for example, *Aedes aegypti*, *Aedes albopictus*, *Aedes taeniorhynchus*, *Anopheles* spp., *Calliphora erythrocephala*, *Chrysozona pluvialis*, *Culex quinquefasciatus*, *Culex pipiens*, *Culex tarsalis*, *Drosophila* spp., *Fannia canicularis*, *Musca domestica*, *Phlebotomus* spp., *Sarcophaga carnaria*, *Simulium* spp., *Stomoxys calcitrans*, *Tipula paludosa*.

From the order of the Lepidoptera, for example, *Achroia grisella*, *Galleria mellonella*, *Plodia interpunctella*, *Tinea cloacella*, *Tinea pellionella*, *Tineola bisselliella*.

From the order of the Siphonaptera, for example, *Ctenocephalides canis*, *Ctenocephalides felis*, *Pulex irritans*, *Tunga penetrans*, *Xenopsylla cheopis*.

From the order of the Hymenoptera, for example, *Camponotus herculeanus*, *Lasius fuliginosus*, *Lasius niger*, *Lasius umbratus*, *Monomorium pharaonis*, *Paravespula* spp., *Tetramorium caespitum*.

From the order of the Anoplura, for example, *Pediculus humanus capitis*, *Pediculus humanus corporis*, *Pemphigus* spp., *Phylloera vastatrix*, *Phthirus pubis*.

From the order of the Heteroptera, for example, *Cimex hemipterus*, *Cimex lectularius*, *Rhodinus prolixus*, *Triatoma infestans*.

In the field of domestic insecticides, they are used alone or in combination with other suitable active ingredients, such as phosphoric esters, carbamates, pyrethroids, neonicotinoids, growth regulators or active ingredients from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for scattering or in bait stations.

PREPARATION EXAMPLES

Example 1

2-chloro-2,2-difluoroethylammonium chloride

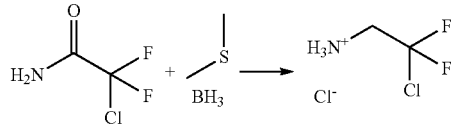

15.12 g (116.7 mmol) of chlorodifluoroacetamide were dissolved in 150 ml of THF under argon and admixed with 8 g (105.3 mmol) of borane-dimethyl sulphide. The mixture was heated under reflux for 1 hour, 40 ml of dilute hydrochloric acid were added slowly, the mixture was heated under reflux for another 1 hour, cooled with an ice bath, and admixed with ether, dilute sodium hydroxide solution and aqueous citric acid to pH=9, the aqueous phase was extracted a total of three times with ether, the combined organic phases were dried over sodium sulphate, the resulting solution was admixed with approx 80 ml of 2M HCl in ether, and the precipitate formed was filtered off with suction and dried on a rotary evaporator.

Yield: 5.99 g (33% of theory)

N-(2-chloro-2,2-difluoroethyl)-4-methyl-2-pyridin-3-ylthiazole-5-carboxamide

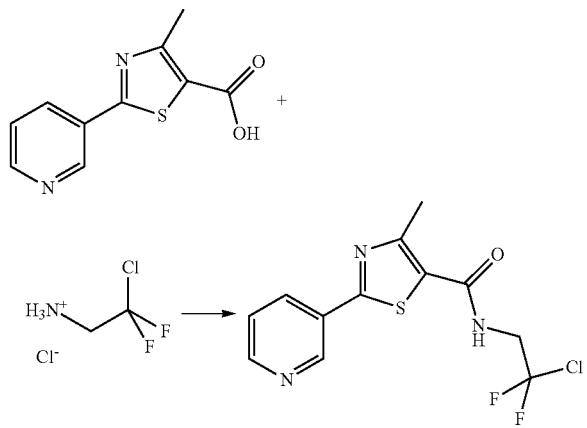

330 mg (1.50 mmol) of the thiazolecarboxylic acid and 2.52 g (19.5 mmol) of N,N-diisopropylethylamine were initially charged in 70 ml of acetonitrile and admixed with 458 mg (1.8 mmol) of bis(2-oxo-3-oxazolidinyl)phosphinic chloride (Bop-Cl) while stirring. After 20 minutes, 455 mg (3 mmol) of the amine hydrochloride were added, and the mixture was stirred at room temperature for 16 hours. For workup, the mixture was concentrated under reduced pressure, partitioned between ethyl acetate and sodium chloride solution/phosphate buffer solution (pH 7), and the organic phase was dried over sodium sulphate and concentrated under reduced pressure. The residue was purified by chromatography on silica gel (cyclohexane/ethyl acetate).

Yield: 265 mg (51% of theory), log P$^{1)}$ (HCOOH) 1.84

1H NMR (CD3CN): 2.7 (s, 3H) 4.2 (dt, 2H), 7.1 (br, 1H), 7.45 (dd, 1H), 8.2 (m, 1H), 8.75 (m, 1H), 9.1 (m, 1H)

Example 2

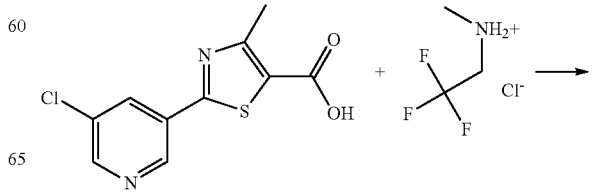

-continued

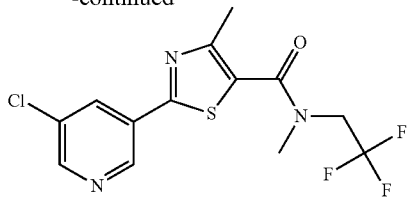

150 mg (0.589 mmol) of the thiazolecarboxylic acid and 989 mg (7.66 mmol) of N,N-diisopropylethylamine were initially charged in 30 ml of acetonitrile and admixed with 179 mg (0.71 mmol) of bis(2-oxo-3-oxazolidinyl)phosphinic chloride (Bop-Cl) while stirring. After 20 minutes, 264 mg (1.77 mmol) of the amine hydrochloride were added and the mixture was stirred at room temperature for 16 hours. For workup, the mixture was concentrated under reduced pressure, partitioned between ethyl acetate and water, and the organic phase was dried over magnesium sulphate and concentrated under reduced pressure.

Yield: 192 mg (90% of theory), log P (HCOOH) 2.72

1H NMR (d6-DMSO): 2.43 (s, 3H), 3.13 (s, 3H), 4.35 (q, 2H), 8.37 (1H, m), 8.73 (1H, m), 9.05 (1H, m) ppm.

Example 3

Stage 1: sodium 2-chloro-2-ethoxycarbonylethoxide

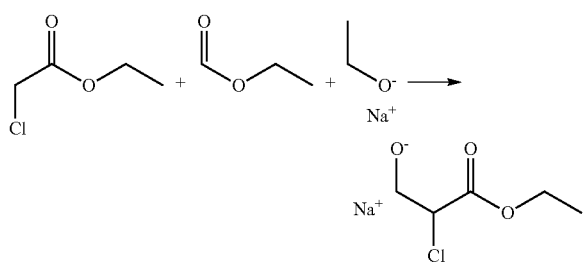

89.31 g (728 mmol) of ethyl chloroacetate and 63.7 g (859.9 mmol) of ethyl formate were dissolved in 500 ml of MTBE. 259.77 g (801 mmol) of an ethanolic solution of sodium ethoxide were added dropwise while stirring. After 16 hours, the supernatant was decanted off from the precipitate formed, the residue was stirred with approx. 500 ml of diethyl ether and filtered with suction, and the solid was washed with a further 500 ml of diethyl ether and dried.

Yield 84 g (66% of theory)

Stage 2: ethyl 2-pyridin-3-ylthiazole-5-carboxylate

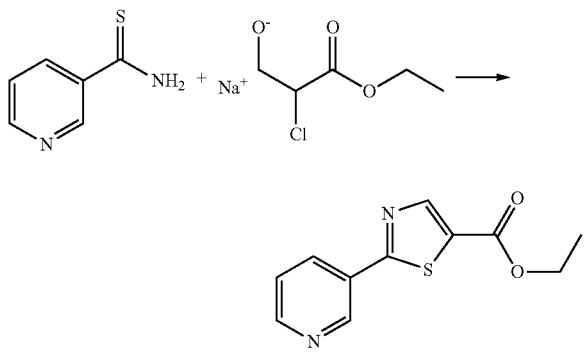

20 g (144.72 mmol) of thionicotinamide were stirred with 50.52 g (289.45 mmol) of sodium 2-chloro-2-ethoxycarbonylethoxide in 600 ml of ethanol at reflux for 24 hours. The solvent was removed under reduced pressure, the residue was admixed with dichloromethane, and the organic phase was washed three times with water and concentrated by evaporation. The residue was recrystallized from dichloromethane/hexane. Further product was isolated from the mother liquor.

Yield 18.66 g (50% of theory), log P (HCOOH) 1.93

Stage 3: 2-pyridin-3-ylthiazole-5-carboxylic acid

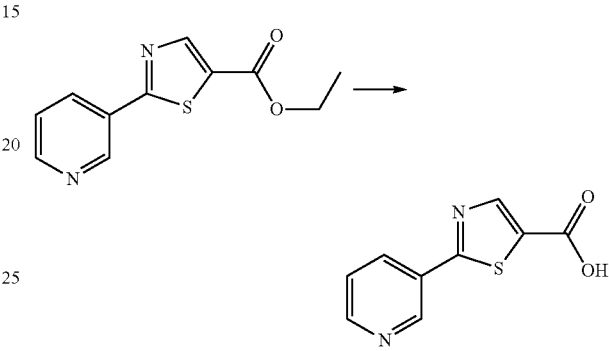

4.03 g (16.5 mmol) of the thiazolecarboxylic ester were initially charged in 60 ml of ethanol, a solution of 5.86 g (66 mmol) of sodium hydroxide in 20 ml of water was added dropwise and the mixture was stirred at room temperature for 16 hours. The ethanol was distilled off and the remaining aqueous solution was acidified with hydrochloric acid. The precipitated product was filtered off with suction and dried.

Yield: 2.57 g (75% of theory), log P (HCOOH): 0.42

Stage 4: 3-(5-chlorocarbonylthiazol-2-yl)pyridinium chloride

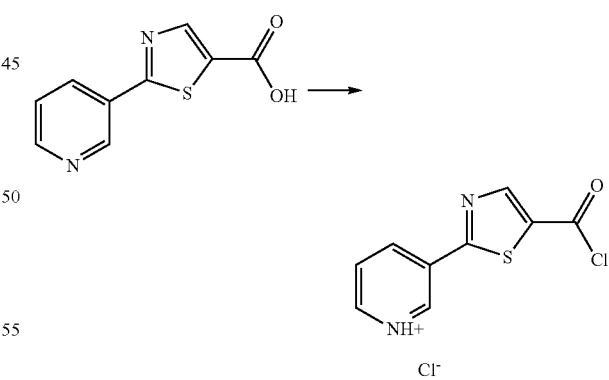

8.50 g (41.21 mmol) of the thiazolecarboxylic acid in 120 ml of toluene together with a few drops of DMF were admixed with 5.1 ml (70 mmol) of thionyl chloride within 30 min, then the mixture was stirred at 60° C. for 3 hours, cooled while argon was passed through the solution for 30 min and cooled in an ice bath for another 30 min, and the precipitate was filtered off with suction, washed with toluene and dried on a rotary evaporator.

Yield: 10.36 g (96% of theory)

Stage 5

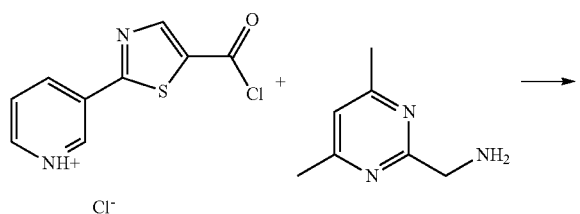

219 mg (0.84 mmol) of the acid chloride were initially charged in 6 ml of dioxane, admixed with 324 mg (2.51 mmol) of N,N-diisopropylethylamine and 138 mg (1.00 mmol) of the pyrimidylmethylamine and stirred at room temperature for 16 hours. For workup, the mixture was concentrated under reduced pressure, the residue was partitioned between ethyl acetate and water, and the organic phase was dried and concentrated.

Yield: 96 mg (34% of theory), log P (HCOOH) 1.19

1H NMR (d6-DMSO): 2.40 (s, 6H), 4.58 (m, 2H), 7.1 (m, 1H), 7.55 (m, 1H), 8.35 (m, 1H), 8.55 (s, 1H), 8.70 (m, 1H), 9.10 (m, 1H), 9.15 (m, 1H) ppm.

Example 4

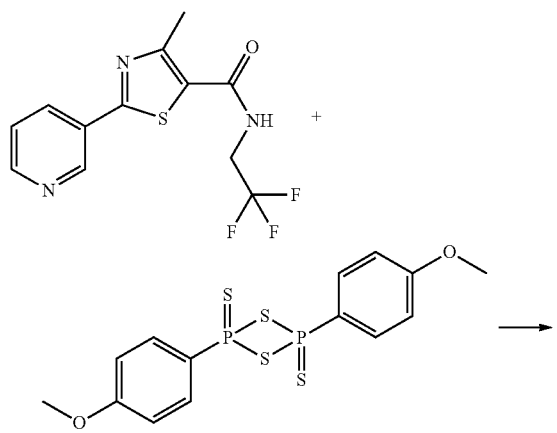

600 mg (1.99 mmol) of the thiazolecarboxamide and 443 mg (1.10 mmol) of 4-methoxyphenyldithiophosphonic anhydride were heated to reflux under argon in 60 ml of toluene for 16 hours. For workup, the mixture was partitioned between sodium hydrogencarbonate solution and ethyl acetate, and the organic phase was dried and concentrated. The residue was purified by chromatography on silica gel (dichloromethane/ethyl acetate).

Yield: 590 mg (92% of theory), log P (HCOOH) 2.39

1H NMR (d6-DMSO): 2.54 (s, 3H), 4.65 (q, 2H), 7.50 (m, 1H), 8.25 (m, 1H), 8.65 (m, 1H), 9.10 (m, 1H) ppm.

Example 5

Stage 1

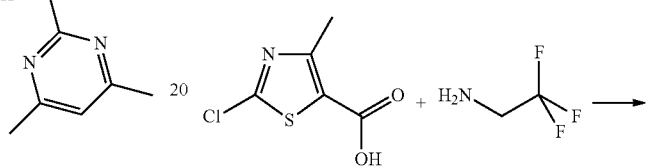

2.22 g (12.5 mmol) of the chlorothiazolecarboxylic acid and 21 g (162 mmol) of diisopropylethylamine in 50 ml of acetonitrile were admixed with 3.82 g (15 mmol) of bis(2-oxo-3-oxazolidinyl)phosphinic chloride (Bop-Cl) while stirring. After 20 minutes, 1.857 g (18.75 mmol) of the amine were added and the mixture was stirred at room temperature for 16 hours. For workup, the mixture was partitioned between water and ethyl acetate, and the organic phase was dried and concentrated. The residue was purified by chromatography on silica gel (dichloromethane/ethyl acetate).

Yield: 1.10 g (34% of theory), log P (HCOOH) 1.97

Stage 2

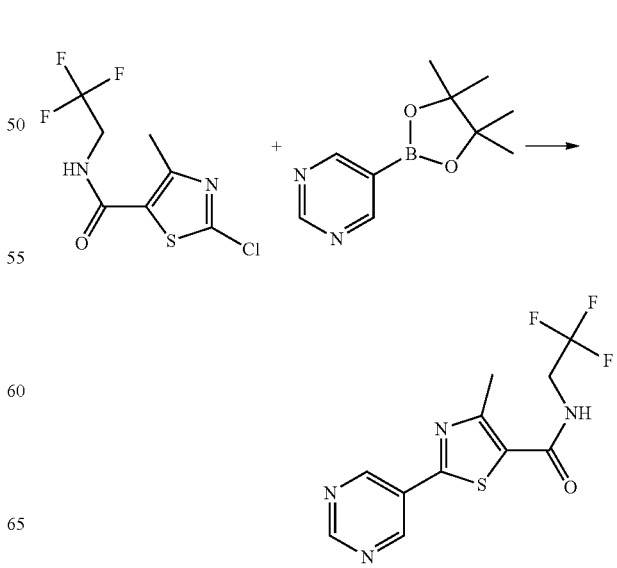

326 mg (1.26 mmol) of the chlorothiazolecarboxamide from Stage 1, 200 mg (0.97 mmol) of the pyrimidylboric ester and 21 mg (0.029 mmol) of 1,1'-bis(diphenylphosphino)ferrocene-palladium(II) chloride were initially charged in 10 ml of dimethoxyethane. 1.45 ml of 2M potassium carbonate solution were added and the mixture was stirred under argon at 80° C. for 4 h. For workup, the mixture was partitioned between water and dichloromethane, and the organic phase was dried over magnesium sulphate and concentrated. The residue was purified by chromatography on silica gel (dichloromethane/ethyl acetate).

Yield: 64 mg (21% of theory), log P (HCOOH) 1.61

1H NMR (d6-DMSO): 2.60 (s, 3H), 4.05 (m, 2H), 8.85 (m, 1H), 9.25 (m, 2H).

Example 6

Stage 1

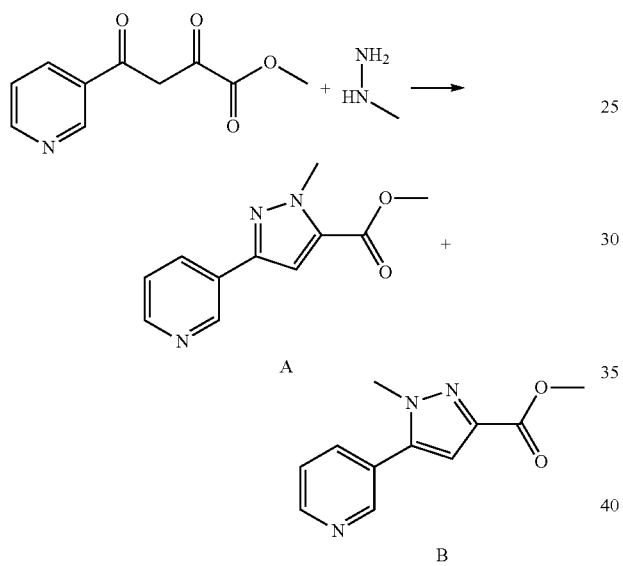

A

B 15.0 g (72.4 mmol) of the pyridine diketo ester and 3.34 g (72.4 mmol) of methylhydrazine were heated under reflux in 300 ml of ethanol for 2 hours. Then the mixture was concentrated under reduced pressure and the isomers were separated by chromatography on silica gel (eluent: cyclohexane/ethyl acetate).

Yield:

6.55 g (41% of theory) of the desired isomer A, log P (HCOOH) 0.84 (used further in the next stage)

2.23 g (14% of theory) of the other isomer B, log P (HCOOH) 0.77

Stage 2

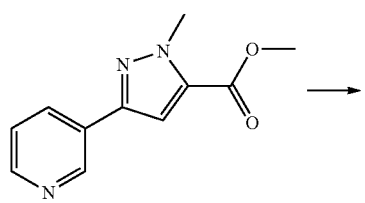

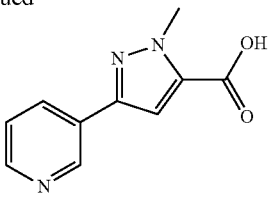

6.55 g (30.15 mmol) of the pyrazolecarboxylic ester were dissolved in a mixture of 400 ml of THF (tetrahydrofuran) and 250 ml of water, admixed with a solution of 2.53 g (60.31 mmol) of lithium hydroxide monohydrate in 150 ml of water and stirred at room temperature for 16 hours. For workup, the THF was removed under reduced pressure and the precipitated product was filtered off with suction and dried.

Yield: 6.08 g (99% of theory)

Stage 3

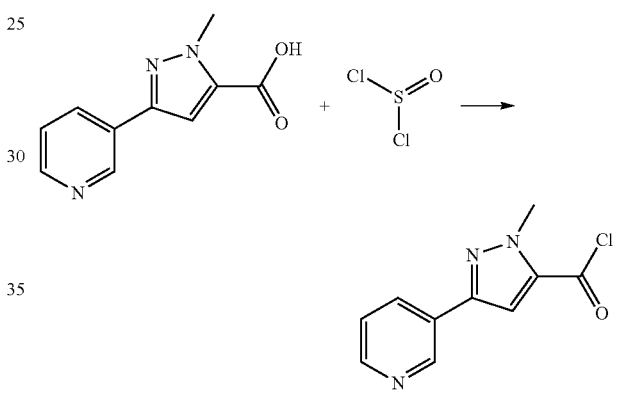

2.0 g (9.84 mmol) of the pyrazolecarboxylic acid were heated under reflux in 50 ml of thionyl chloride for 2 hours, and concentrated.

Yield: 2.13 g (91% of theory)

Stage 4

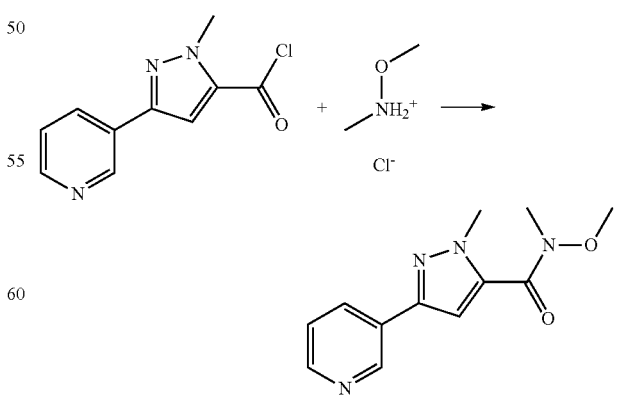

3.00 g (13.5 mmol) of the pyrazolyl chloride were stirred in 100 ml of dioxane with 7.00 g (54.1 mmol) of N,N- diisopropylethylamine and 1.58 g (16.2 mmol) of the amine hydrochloride at room temperature for 16 hours. For workup, the mixture was concentrated and the residue was purified by chromatography on silica gel (eluent: cyclohexane/ethyl acetate).

Yield: 1.92 g (56% of theory), log P (HCOOH) 0.49

1H NMR (d6-DMSO): 3.31 (s, 3H), 3.70 (s, 3H), 4.02 (s, 3H), 7.20 (s, 1H), 7.40 (m, 1H), 8.15 (m, 1H), 8.50 (m, 1H), 9.02 (m, 1H).

Example 7

Stage 1: ethyl oxo[N'-(pyridine-3-carbonyl)hydrazino]acetate

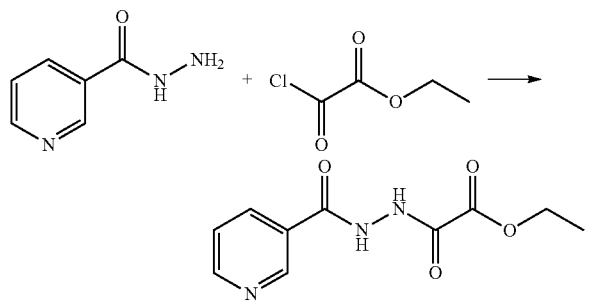

28.0 g (204 mmol) of nicotinic hydrazide were dissolved in 700 ml of DMF by gentle heating, then 52.5 g (518 mmol) of triethylamine were added and, while cooling with an ice bath, a solution of 31.7 g (232 mmol) of oxalyl chloride in 40 ml of dichloromethane was added dropwise. The mixture was stirred for 15 minutes and concentrated by evaporation, and the residue was partitioned between water (pH7) and chloroform/isopropanol (10:1). The organic phase was dried and concentrated under reduced pressure.

Yield: 59.0 g of crude product, converted in the next stage without further purification.

Stage 2: ethyl 5-pyridin-3-yl[1,3,4]thiadiazole-2-carboxylate

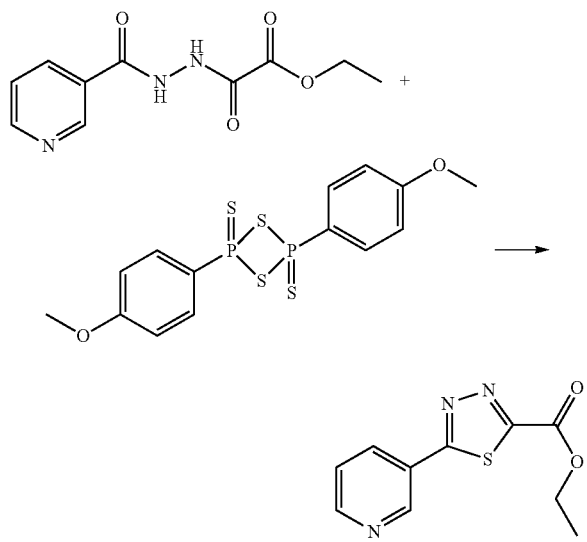

59.0 g (248 mmol) of the hydrazone and 57.3 g (141 mmol) of methoxyphenyldithiophosphonic anhydride were heated to reflux in 500 ml of toluene for 4 hours. For workup, the mixture was concentrated under reduced pressure and purified by means of chromatography on silica gel (cyclohexane/acetone).

Yield: 15.5 g (26% of theory), log P (HCOOH) 1.41

Stage 3: sodium 5-pyridin-3-yl[1,3,4]thiadiazole-2-carboxylate

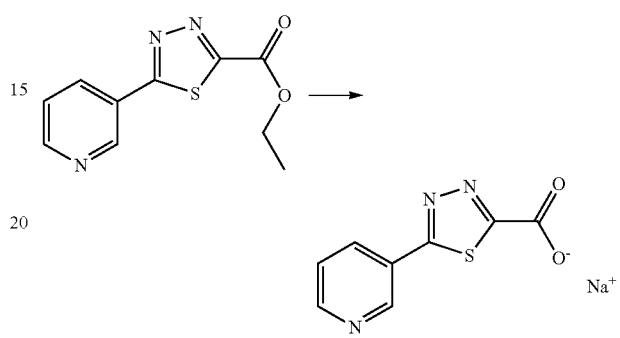

1.5 g (6.37 mmol) of the thiadiazolecarboxylic ester and 2.3 ml (6.3 mmol) of a 21% solution of sodium ethoxide in ethanol were stirred in a mixture of 23 ml of ethanol and 7.5 ml of water at room temperature for 30 minutes, and stirred for another 10 min with ice bath cooling. The precipitated product was filtered off with suction, washed twice with ether and dried on a rotary evaporator.

Yield: 1.35 g (92% of theory)

Stage 4: N,N-dimethyl-5-pyridin-3-yl[1,3,4]thiadiazole-2-carboxamide

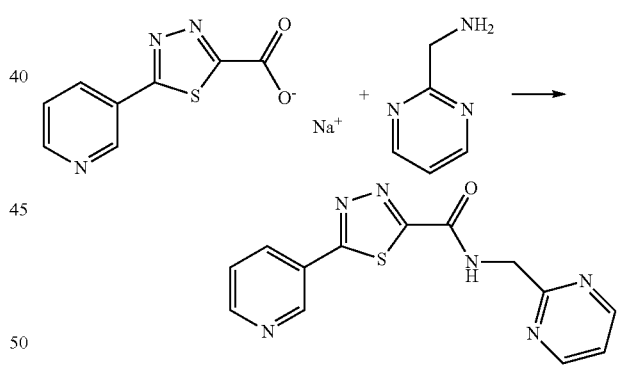

To 0.50 g (2.18 mmol) of the thiadiazolecarboxylic salt in a mixture of 20 ml of THF and 2 ml of DMF (dimethylformamide) were added dropwise 0.498 g (3.92 mmol) of oxalyl chloride. After the evolution of gas had ended, 0.726 g (7.17 mmol) of triethylamine and 0.476 g (4.36 mmol) of the amine were added, and the mixture was stirred at room temperature for 16 hours. For workup, the mixture was concentrated under reduced pressure and partitioned between water and chloroform/isopropanol (10:1), and the organic phase was dried, concentrated under reduced pressure and purified by means of chromatography on silica gel (ethyl acetate, acetone).

Yield: 0.14 g (19% of theory), log P (HCOOH) 0.85; log P (pH=7.5) 0.85

1H NMR (d6-DMSO): 4.25 (m, 2H), 7.4 (t, 1H), 7.6 (m, 1H), 8.4 (m, 1H), 8.8 (m, 3H), 9.2 (m, 1H), 9.4 (br, 1H)

Example 8

N,N-dimethyl-5-pyridin-3-yl[1,3,4]thiadiazole-2-carboxamide

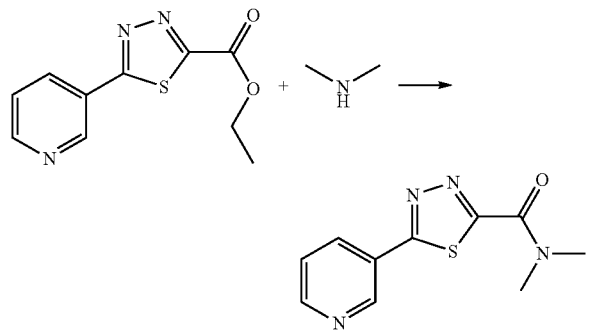

0.3 g (1.25 mmol) of the thiadiazole ester was stirred with 2.5 ml (14 mmol) of a 5.6-molar solution of dimethylamine in ethanol in 15 ml of ethanol at 105° C. for 1 hour in a closed reaction vessel. The mixture was concentrated by evaporation, dissolved in 10 ml of hot 1,1,1-benzotrifluoride, boiled briefly with a little activated carbon which was hot-filtered off, and allowed to cool, and the precipitate formed was filtered off with suction and dried on a rotary evaporator.

Yield 0.1 g (32% of theory) log P (HCOOH) 0.95

1H NMR (d6-DMSO): 3.1 (s, 3H, under DMSO), 3.4 (2, 3H), 7.4 (m, 1H), 8.4 (m, 1H), 8.8 (m, 3H), 9.2 (m, 1H)

The table which follows lists further inventive compounds.

TABLE 1

(NMR data for some compounds are listed in Table 2 which follows)

| Compound No. | Formula | logP [1] (HCOOH) | [M + 1] from LC-MS |
|---|---|---|---|
| Preparation Example 1 | | 1.84 | 318.1 |
| Preparation Example 2 | | 2.72 | 350.0 |
| Preparation Example 3 | | 1.19 | 326.1 |
| Preparation Example 4 | | 2.38 | 318.0 |

TABLE 1-continued (NMR data for some compounds are listed in Table 2 which follows)

| Compound No. | Formula | logP [1] (HCOOH) | [M + 1] from LC-MS |
|---|---|---|---|
| Preparation Example 5 | | 1.61 | 289.1 |
| Preparation Example 6 | | 0.49 | 247.1 |
| Preparation Example 7 | | 0.85 | 299.1 |
| Preparation Example 8 | | 0.95 | 235.1 |
| 9 | | 2.15 | 320.1 |
| 10 | | 1.39 | |

TABLE 1-continued
(NMR data for some compounds are listed in Table 2 which follows)
| Compound No. | Formula | logP [1] (HCOOH) | [M + 1] from LC-MS |
|---|---|---|---|
| 11 | 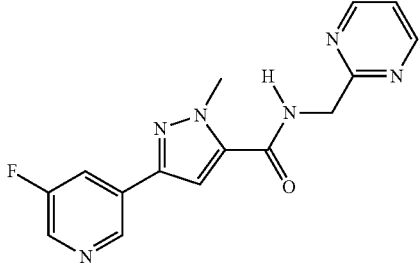 [SMILES: Cn1nc(-c2cncc(F)c2)cc1C(=O)NCc1ncccn1] | 1.24 | |
| 12 | 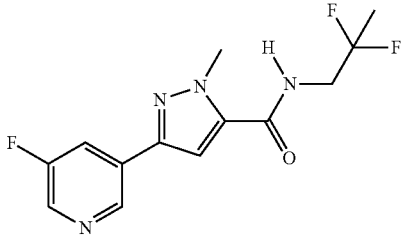 [SMILES: Cn1nc(-c2cncc(F)c2)cc1C(=O)NCC(C)(F)F] | 1.89 | |
| 13 | 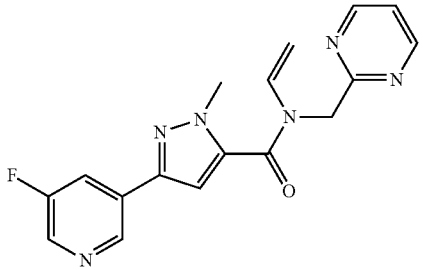 [SMILES: C=CN(Cc1ncccn1)C(=O)c1cc(-c2cncc(F)c2)nn1C] | 1.75 | |
| 14 | 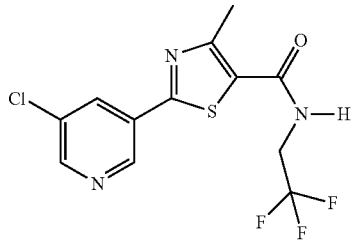 [SMILES: Cc1nc(-c2cncc(Cl)c2)sc1C(=O)NCC(F)(F)F] | 2.50 | |
| 15 | 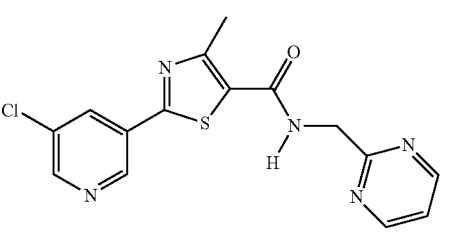 [SMILES: Cc1nc(-c2cncc(Cl)c2)sc1C(=O)NCc1ncccn1] | 1.69 | |

TABLE 1-continued (NMR data for some compounds are listed in Table 2 which follows)

| Compound No. | Formula | logP [1] (HCOOH) | [M + 1] from LC-MS |
|---|---|---|---|
| 16 | | 2.61 | |
| 17 | | 1.80 | |
| 18 | | 1.87 | |
| 19 | | 1.49 | |
| 20 | | 2.75 | |
| 21 | | 1.72 | |

TABLE 1-continued (NMR data for some compounds are listed in Table 2 which follows)

| Compound No. | Formula | logP [1] (HCOOH) | [M + 1] from LC-MS |
|---|---|---|---|
| 22 | | 1.05 | |
| 23 | | 1.00 | |
| 24 | | 0.91 | 281.1 |
| 25 | | 0.65 | 267.1 |
| 26 | | 0.54 | 299.1 |

TABLE 1-continued (NMR data for some compounds are listed in Table 2 which follows)

| Compound No. | Formula | logP [1] (HCOOH) | [M + 1] from LC-MS |
|---|---|---|---|
| 27 | | 0.99 | 295.1 |
| 28 | | 0.25 | 295.1 |
| 29 | | 0.56 | 284.1 |
| 30 | | 1.09 | |
| 31 | | 1.04 | |
| 32 | | 1.53 | |

TABLE 1-continued (NMR data for some compounds are listed in Table 2 which follows)

| Compound No. | Formula | logP [1] (HCOOH) | [M + 1] from LC-MS |
|---|---|---|---|
| 33 | | 0.72 | |
| 34 | | 1.84 | 328.0 |
| 35 | | 1.65 | 312.1 |
| 36 | | 1.59 | 298.1 |
| 37 | | 1.24 | 326.1 |
| 38 | | 1.21 | 316.1 |

TABLE 1-continued (NMR data for some compounds are listed in Table 2 which follows)

| Compound No. | Formula | logP [1] (HCOOH) | [M + 1] from LC-MS |
|---|---|---|---|
| 39 | | 1.63 | 302.0 |
| 40 | | 1.05 | 312.1 |
| 41 | | 1.48 | 298.0 |
| 42 | | 1.81 | 316.1 |
| 43 | | 1.69 | 348.0 |
| 44 | | 1.54 | 293.1 |

TABLE 1-continued (NMR data for some compounds are listed in Table 2 which follows)

| Compound No. | Formula | logP [1] (HCOOH) | [M + 1] from LC-MS |
|---|---|---|---|
| 45 | | 2.21 | 336.1 |
| 46 | | 0.91 | 234.1 |
| 47 | | 1.41 | 301.1 |
| 48 | | 2.05 | 330.1 |
| 49 | | 1.27 | 333.1 |
| 50 | | 0.80 | 320.1 |
| 51 | | 1.30 | 318.1 |

TABLE 1-continued (NMR data for some compounds are listed in Table 2 which follows)

| Compound No. | Formula | logP [1] (HCOOH) | [M + 1] from LC-MS |
|---|---|---|---|
| 52 | | 1.48 | |
| 53 | | 1.11 | 266.1 |
| 54 | | 1.16 | 278.1 |
| 55 | | 1.03 | 234.0 |
| 56 | Chiral | 1.68 | 307.1 |
| 57 | | 1.34 | 284.1 |

TABLE 1-continued (NMR data for some compounds are listed in Table 2 which follows)

| Compound No. | Formula | logP 1) (HCOOH) | [M + 1] from LC-MS |
|---|---|---|---|
| 58 | | 2.77 | 388.1 |
| 59 | | 0.62 | 220.1 |
| 60 | | 1.14 | 301.1 |
| 61 | | 1.23 | |
| 62 | | 1.34 | |
| 63 | | 1.85 | |

TABLE 1-continued
(NMR data for some compounds are listed in Table 2 which follows)
| Compound No. | Formula | logP [1] (HCOOH) | [M + 1] from LC-MS |
|---|---|---|---|
| 64 | 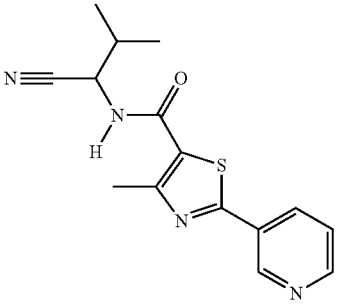 [SMILES: Cc1nc(-c2cccnc2)sc1C(=O)NC(C#N)C(C)C] | 1.57 | |
| 65 | 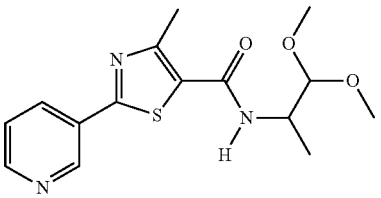 [SMILES: COC(OC)C(C)NC(=O)c1sc(-c2cccnc2)nc1C] | 1.45 | |
| 66 | 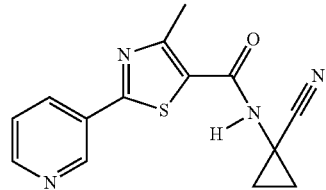 [SMILES: Cc1nc(-c2cccnc2)sc1C(=O)NC1(C#N)CC1] | 1.20 | |
| 67 | 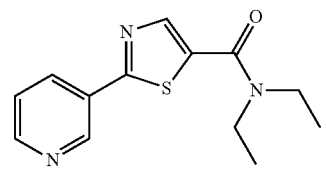 [SMILES: CCN(CC)C(=O)c1cnc(-c2cccnc2)s1] | 1.46 | |
| 68 | 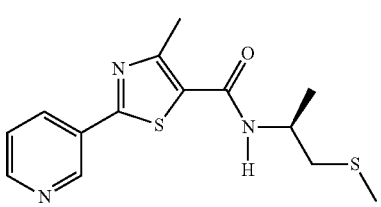 [SMILES: CSC[C@H](C)NC(=O)c1sc(-c2cccnc2)nc1C] | 1.65 | |
| 69 | 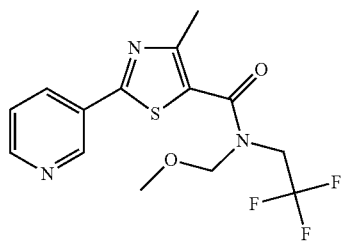 [SMILES: COCN(CC(F)(F)F)C(=O)c1sc(-c2cccnc2)nc1C] | 2.06 | |

TABLE 1-continued (NMR data for some compounds are listed in Table 2 which follows)

| Compound No. | Formula | logP [1] (HCOOH) | [M + 1] from LC-MS |
|---|---|---|---|
| 70 | | 1.14 | |
| 71 | | 1.71 | |
| 72 | | 0.29 | |
| 73 | | 2.05 | |
| 74 | | 0.94 | |
| 75 | | 1.34 | |
| 76 | | 1.13 | |

TABLE 1-continued (NMR data for some compounds are listed in Table 2 which follows)

| Compound No. | Formula | logP [1] (HCOOH) | [M + 1] from LC-MS |
|---|---|---|---|
| 77 | | 1.15 | |
| 78 | | 1.31 | |
| 79 | | 0.88 | |
| 80 | | 1.50 | |
| 81 | | 0.73 | |
| 82 | | 1.75 | |

TABLE 1-continued (NMR data for some compounds are listed in Table 2 which follows)

| Compound No. | Formula | logP [1] (HCOOH) | [M + 1] from LC-MS |
|---|---|---|---|
| 83 | | 1.16 | |
| 84 | | 1.36 | |
| 85 | | 1.23 | |
| 86 | | 1.94 | |
| 87 | | 1.10 | |
| 88 | | 1.31 | |
| 89 | | 2.61 | |

TABLE 1-continued (NMR data for some compounds are listed in Table 2 which follows)

| Compound No. | Formula | logP [1] (HCOOH) | [M + 1] from LC-MS |
|---|---|---|---|
| 90 | | 0.78 | |
| 91 | | 1.02 | |
| 92 | | 1.27 | |
| 93 | | 1.19 | |
| 94 | | 1.76 | |

TABLE 1-continued (NMR data for some compounds are listed in Table 2 which follows)

| Compound No. | Formula | logP [1] (HCOOH) | [M + 1] from LC-MS |
|---|---|---|---|
| 95 | | 1.24 | |
| 96 | | 1.98 | |
| 97 | | 1.42 | |
| 98 | | 1.45 | |
| 99 | | 1.28 | |
| 100 | | 2.17 | |

TABLE 1-continued (NMR data for some compounds are listed in Table 2 which follows)

| Compound No. | Formula | logP [1] (HCOOH) | [M + 1] from LC-MS |
|---|---|---|---|
| 101 | | 1.33 | |
| 102 | | 1.30 | |
| 103 | | 1.40 | |
| 104 | | 1.64 | |
| 105 | | 1.23 | |
| 106 | | 0.61 | |

TABLE 1-continued (NMR data for some compounds are listed in Table 2 which follows)

| Compound No. | Formula | logP [1] (HCOOH) | [M + 1] from LC-MS |
|---|---|---|---|
| 107 | | 1.03 | |
| 108 | | 1.78 | |
| 109 | | 1.61 | |
| 110 | | 1.22 | |
| 111 | | 1.45 | |

TABLE 1-continued
(NMR data for some compounds are listed in Table 2 which follows)
| Compound No. | Formula | logP [1] (HCOOH) | [M + 1] from LC-MS |
|---|---|---|---|
| 112 | 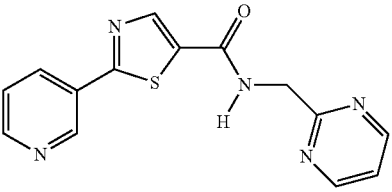 | 0.81 | |
| 113 | 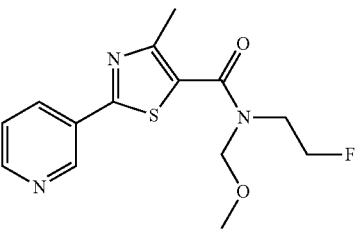 [SMILES: COCN(CCF)C(=O)c1sc(-c2cccnc2)nc1C] | 1.46 | |
| 114 | 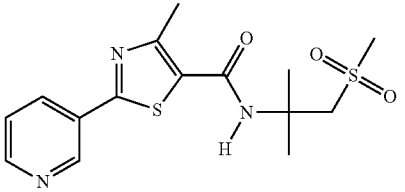 [SMILES: Cc1nc(-c2cccnc2)sc1C(=O)NC(C)(C)CS(C)(=O)=O] | 1.28 | |
| 115 | 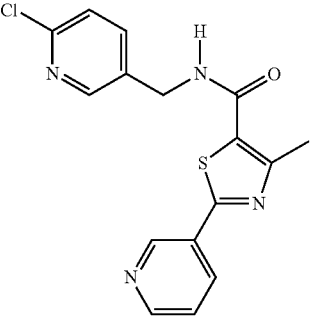 [SMILES: Cc1nc(-c2cccnc2)sc1C(=O)NCc1ccc(Cl)nc1] | 1.71 | |
| 116 | 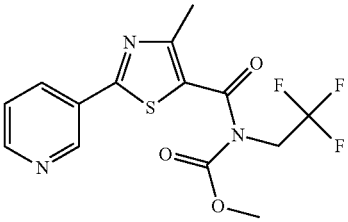 [SMILES: COC(=O)N(CC(F)(F)F)C(=O)c1sc(-c2cccnc2)nc1C] | 2.46 | |
| 117 | 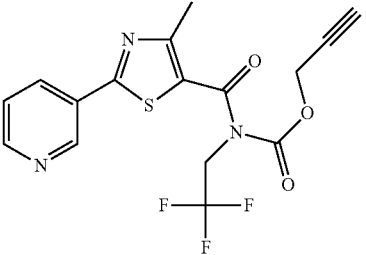 [SMILES: C#CCOC(=O)N(CC(F)(F)F)C(=O)c1sc(-c2cccnc2)nc1C] | 2.63 | |

TABLE 1-continued (NMR data for some compounds are listed in Table 2 which follows)

| Compound No. | Formula | logP [1] (HCOOH) | [M + 1] from LC-MS |
|---|---|---|---|
| 118 | | 1.14 | |
| 119 | | 1.71 | |
| 120 | | 1.75 | |
| 121 | | 1.98 | |
| 122 | | 1.13 | |
| 123 | | 2.42 | |

TABLE 1-continued (NMR data for some compounds are listed in Table 2 which follows)

| Compound No. | Formula | logP [1] (HCOOH) | [M + 1] from LC-MS |
|---|---|---|---|
| 124 | | 2.11 | |
| 125 | | 1.69 | |
| 126 | | 0.90 | |
| 127 | | 0.98 | |
| 128 | | 0.75 | |
| 129 | | 1.23 | |

TABLE 1-continued (NMR data for some compounds are listed in Table 2 which follows)

| Compound No. | Formula | logP [1] (HCOOH) | [M + 1] from LC-MS |
|---|---|---|---|
| 130 | | 1.38 | |
| 131 | | 2.56 | |
| 132 | | 1.51 | |
| 133 | | 0.80 | |
| 134 | | 0.41 | |
| 135 | | 0.46 | |

TABLE 1-continued (NMR data for some compounds are listed in Table 2 which follows)

| Compound No. | Formula | logP [1] (HCOOH) | [M + 1] from LC-MS |
|---|---|---|---|
| 136 | | 1.17 | |
| 137 | | 1.28 | |
| 138 | | 1.09 | |
| 139 | | 2.47 | |
| 140 | | 1.93 | |

TABLE 1-continued (NMR data for some compounds are listed in Table 2 which follows)

| Compound No. | Formula | logP [1] (HCOOH) | [M + 1] from LC-MS |
|---|---|---|---|
| 141 | | 2.10 | |
| 142 | | 1.56 | |
| 143 | | 1.42 | |
| 144 | | 1.45 | |
| 145 | | 1.38 | |
| 146 | | 2.48 | |

TABLE 1-continued (NMR data for some compounds are listed in Table 2 which follows)

| Compound No. | Formula | logP [1] (HCOOH) | [M + 1] from LC-MS |
|---|---|---|---|
| 147 | | 1.45 | |
| 148 | | 1.38 | |
| 149 | | 2.48 | |
| 150 | | 1.19 | |
| 151 | | 1.01 | |

TABLE 1-continued (NMR data for some compounds are listed in Table 2 which follows)

| Compound No. | Formula | logP [1] (HCOOH) | [M + 1] from LC-MS |
|---|---|---|---|
| 152 | | 2.95 | |
| 153 | | 2.43 | |
| 154 | | 1.21 | |
| 155 | | 1.48 | |
| 156 | | 1.66 | |

TABLE 1-continued (NMR data for some compounds are listed in Table 2 which follows)

| Compound No. | Formula | logP [1] (HCOOH) | [M + 1] from LC-MS |
|---|---|---|---|
| 157 | | 1.69 | |
| 158 | | 1.48 | |
| 159 | | 1.26 | |
| 160 | | 1.27 | |
| 161 | | 1.26 | |
| 162 | | 1.78 | |

TABLE 1-continued (NMR data for some compounds are listed in Table 2 which follows)

| Compound No. | Formula | logP [1] (HCOOH) | [M + 1] from LC-MS |
|---|---|---|---|
| 163 | | 1.10 | |
| 164 | | 1.52 | |
| 165 | | 1.06 | |
| 166 | | 1.44 | |
| 167 | | 0.97 | |

TABLE 1-continued (NMR data for some compounds are listed in Table 2 which follows)

| Compound No. | Formula | logP [1] (HCOOH) | [M + 1] from LC-MS |
|---|---|---|---|
| 168 | | 1.89 | |
| 169 | | 0.69 | |
| 170 | | 1.68 | |
| 171 | | 2.30 | |
| 172 | | 1.63 | |
| 173 | | 1.50 | |

TABLE 1-continued (NMR data for some compounds are listed in Table 2 which follows)

| Compound No. | Formula | logP [1] (HCOOH) | [M + 1] from LC-MS |
|---|---|---|---|
| 174 | | 1.44 | |
| 175 | | 1.02 | |
| 176 | | 1.19 | |
| 177 | | 1.41 | |
| 178 | | 1.65 | |

TABLE 1-continued (NMR data for some compounds are listed in Table 2 which follows)

| Compound No. | Formula | logP [1]) (HCOOH) | [M + 1] from LC-MS |
|---|---|---|---|
| 179 | | 1.68 | |
| 180 | | 1.33 | |
| 181 | | 2.58 | |
| 182 | | 2.24 | |
| 183 | | 1.53 | |
| 184 | | 1.05 | |

TABLE 1-continued (NMR data for some compounds are listed in Table 2 which follows)

| Compound No. | Formula | logP [1] (HCOOH) | [M + 1] from LC-MS |
|---|---|---|---|
| 185 | | 2.91 | |
| 186 | | 1.77 | |
| 187 | | 1.64 | |
| 188 | | 1.45 | |
| 189 | | 2.13 | |
| 190 | | 1.77 | |

TABLE 1-continued
(NMR data for some compounds are listed in Table 2 which follows)
| Compound No. | Formula | logP [1] (HCOOH) | [M + 1] from LC-MS |
|---|---|---|---|
| 191 | 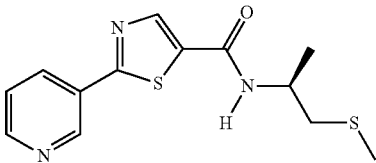 [SMILES: CSC[C@H](C)NC(=O)c1cnc(-c2cccnc2)s1] | 1.53 | |
| 192 | 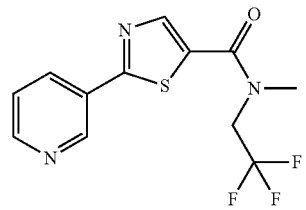 [SMILES: CN(CC(F)(F)F)C(=O)c1cnc(-c2cccnc2)s1] | 1.59 | |
| 193 | 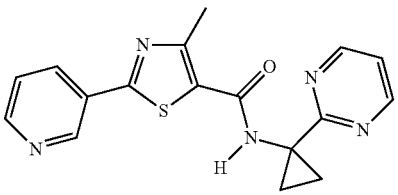 [SMILES: Cc1nc(-c2cccnc2)sc1C(=O)NC1(c2ncccn2)CC1] | 1.21 | |
| 194 | 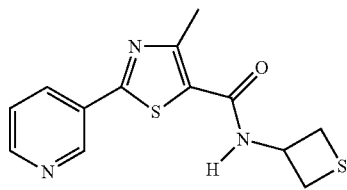 [SMILES: Cc1nc(-c2cccnc2)sc1C(=O)NC1CSC1] | 1.47 | |
| 195 | 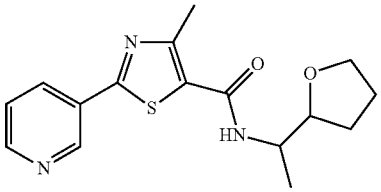 [SMILES: Cc1nc(-c2cccnc2)sc1C(=O)NC(C)C1CCCO1] | 1.50 | |
| 196 | 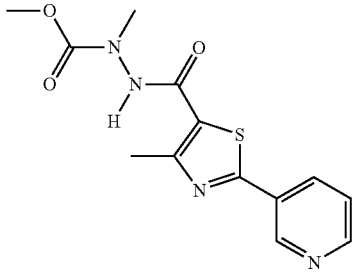 [SMILES: COC(=O)N(C)NC(=O)c1sc(-c2cccnc2)nc1C] | 1.23 | |

TABLE 1-continued (NMR data for some compounds are listed in Table 2 which follows)

| Compound No. | Formula | logP [1] (HCOOH) | [M + 1] from LC-MS |
|---|---|---|---|
| 197 | | 1.48 | |
| 198 | | 1.31 | 338.0 |
| 199 | | 1.44 | |
| 200 | | 1.01 | |
| 201 | | 1.37 | |

TABLE 1-continued (NMR data for some compounds are listed in Table 2 which follows)

| Compound No. | Formula | logP [1] (HCOOH) | [M + 1] from LC-MS |
|---|---|---|---|
| 202 | (structure: 4-methyl-2-(pyridin-3-yl)thiazole-5-carboxamide with N-piperidinyl hydrazide) | | 1.39 |
| 203 | (structure: 4-methyl-2-(pyridin-3-yl)thiazole-5-carboxamide with N-morpholinyl hydrazide) | | 1.23 |
| 204 | (structure: 2-oxo-oxazolidinyl hydrazide of 4-methyl-2-(pyridin-3-yl)thiazole-5-carboxamide) | | 1.11 |

TABLE 2

| Compound No. | NMR data. chem. shift in ppm. |
|---|---|
| 1 | CD$_3$CN: 2.7 (s, 3H) 4.2 (dt, 2H), 7.1 (br, 1H), 7.45 (dd, 1H), 8.2 (m, 1H), 8.75 (m, 1H), 9.1 (m, 1H) |
| 2 | d$_6$-DMSO: 2.43 (s, 3H), 3.13 (s, 3H), 4.35 (q, 2H), 8.37 (m, 1H), 8.73 (m, 1H), 9.05 (m, 1H) |
| 3 | d$_6$-DMSO: 2.40 (s, 6H), 4.58 (m, 2H), 7.1 (m, 1H), 7.55 (m, 1H), 8.35 (m, 1H), 8.55 (s, 1H), 8.70 (m, 1H), 9.10 (m, 1H), 9.15 (m, 1H) |
| 4 | d$_6$-DMSO: 2.54 (s, 3H), 4.65 (q, 2H), 7.50 (m, 1H), 8.25 (m, 1H), 8.65 (m, 1H), 9.10 (m, 1H) |
| 5 | d$_6$-DMSO: 2.60 (s, 3H), 4.05 (m, 2H), 8.85 (m, 1H), 9.25 (m, 2H) |
| 6 | d$_6$-DMSO: 3.31 (s, 3H), 3.70 (s, 3H), 4.02 (s, 3H), 7.20 (s, 1H), 7.40 (m, 1H), 8.15 (m, 1H), 8.50 (m, 1H), 9.02 (m, 1H) |
| 7 | d$_6$-DMSO: 4.25 (m, 2H), 7.4 (t, 1H), 7.6 (m, 1H), 8.4 (m, 1H), 8.8 (m, 3H), 9.2 (m, 1H), 9.4 (br, 1H) |
| 8 | d$_6$-DMS0: 3.1 (s, 3H, under DMSO), 3.4 (s, 3H), 7.4 (m, 1H), 8.4 (m, 1H), 8.8 (m, 1H), 9.2 (m, 1H) |
| 24 | d$_6$-DMSO: 1.65 (t, 3H), 3.7 (m, 2H), 4.11 (s, 3H), 7.4 (m, 2H), 8.1 (m, 1H), 8.5 (m, 1H), 8.8 (m, 1H), 8.95 (m, 1H) |
| 25 | d$_6$-DMSO: 3.7 (m, 2H), 4.11 (s, 3H), 6.11 (m, 1H), 7.45 (m, 1H), 8.1 (m, 1H), 8.5 (m, 1H), 8.8 (m, 1H), 8.95 (m, 1H) |
| 26 | d$_6$-DMSO: 2.57 (s, 3H), 4.1 (s, 3H), 4.55 (m, 2H), 7.48 (m, 1H), 8.1 (m, 1H), 8.54 (m, 1H), 8.95 (m, 1H), 9.05 (m, 1H) |
| 28 | d$_6$-DMSO: 4.1 (s, 3H), 4.65 (s, 2H), 7.4 (m, 2H), 8.1 (m, 1H), 8.5 (m, 1H), 8.8-9.0 (m, 4H) |
| 29 | d$_6$-DMSO: 4.1 (s, 3H), 4.65 (m, 2H), 7.3 (m, 1H), 7.45 (m, 1H), 8.1 (m, 1H), 8.50 (m, 1H), 8.95 (m, 1H), 9.02 (m, 1H) |
| 34 | d$_6$-DMSO: 1.15 (m, 2H), 1.30 (m, 2H), 2.61 (s, 3H), 7.50 (m, 1H), 8.26 (m, 1H), 8.70 (m, 1H), 8.9 (br, 1H), 9.1 (m, 1H) |
| 35 | CD$_3$CN: 1.6 (t, 3H), 2.45 (s, 3H), 3.1 (s, 3H), 3.9 (t, 2H), 7.45 (m, 1H), 8.25 (d, 1H), 8.65 (m, 1H), 9.1 (s, 1H) |
| 36 | CD$_3$CN: 1.7 (t, 3H), 2.7 (s, 3H), 3.8 (td, 2H), 6.8 (br, 1H), 7.45 (m, 1H), 8.2 (d, 1H), 8.65 (m, 1H), 9.1 (s, 1H) |
| 37 | d$_6$-DMSO: 1.55 (d, 3H), 2.55 (s, 3H), 5.2 (m, 1H), 7.38 (m, 1H), 7.52 (m, 1H), 8.25 (m, 1H), 8.50 (m, 1H), 8.7 (m, 1H), 8.75 (m, 2H), 9.1 (m, 1H) |
| 38 | d$_6$-DMSO: 2.58 (s, 3H), 2.63 (s, 3H), 4.52 (s, 2H), 7.50 (m, 1H), 8.28 (m, 1H), 8.65 (m, 1H), 8.80 (br, 1H), 9.1 (m, 1H) |
| 39 | CD$_3$CN: 2.7 (s, 3H), 4.1 (m, 2H), 7.05 (br, 1H), 7.45 (m, 1H), 8.25 (m, 1H), 8.7 (m, 1H), 9.15 (s, 1H) |
| 40 | d$_6$-DMSO: 2.65 (s, 3H), 4.65 (d, 2H), 7.4 (t, 1H), 7.6 (m, 1H), 8.3 (m, 1H), 8.75 (m, 1H), 8.8 (m, 2H), 8.85 (m, 1H), 9.1 (s, 1H) |
| 41 | d$_6$-DMSO: 2.4 (s, 3H), 3.1 (s, 3H), 3.9 (t, 2H), 6.3 (t, 1H), 7.5 (m, 1H), 8.3 (d, 1H), 8.65 (m, 1H), 9.1 (s, 1H) |
| 42 | d$_6$-DMSO: 2.45 (s, 3H), 3.15 (s, 3H), 4.35 (q, 2H), 7.65 (m, 1H), 8.3 (d, 1H), 8.7 (d, 1H), 9.1 (s, 1H) |

TABLE 2-continued

| Compound No. | NMR data. chem. shift in ppm. |
|---|---|
| 43 | d$_6$-DMSO: 2.45 (s, 3H), 3.15 (s, 3H), 4.20 (m, 2H), 7.50 (m, 1H), 8.25 (m, 1H), 8.25 (m, 1H), 8.66 (m, 1H), 9.09 (m, 1H) |
| 45 | CD$_3$CN: 1.50 (s, 6H), 2.15 (s, 3H), 2.5 (s, 3H), 3.02 (s, 3H), 3.25 (s, 2H), 7.45 (m, 1H), 8.20 (m, 1H), 8.61 (m, 1H), 9.1 (m, 1H) |
| 46 | CD$_3$CN: 3.1 (s, 6H), 7.45 (m, 1H), 8.1 (s, 1H), 8.25 (d, 1H), 8.65 (m, 1H), 9.15 (s, 1H) |
| 47 | CD$_3$CN: 1.78 (s, 6H), 2.49 (s, 3H), 3.0 (s, 3H), 7.45 (m, 1H), 8.20 (m, 1H), 8.65 (m, 1H), 9.1 (m, 1H) |
| 48 | CD$_3$CN: 1.1 (t, 3H), 2.43 (s, 3H), 3.5 (m, 2H), 4.22 (m, 2H), 7.45 (m, 1H), 8.22 (m, 1H), 8.65 (m, 1H), 9.1 (m, 1H) |
| 49 | d$_6$-DMSO: 1.35 (d, 3H), 2.60 (s, 3H), 4.0 (m, 2H), 4.32 (m, 2H), 4.58 (m, 1H), 7.50 (m, 1H), 8.25 (m, 1H), 8.30 (m, 1H), 8.65 (m, 1H), 9.1 (m, 1H) |
| 50 | d$_6$-DMSO: 2.60 (s, 3H), 3.23-3.80 (m, 9H), 4.75 (m, 1H), 7.50 (m, 1H), 8.15 (m, 1H), 8.25 (m, 1H), 8.70 (m, 1H), 9.08 (m, 1H) |
| 51 | d$_6$-DMSO: 1.18 (m, 2H), 1.45 (m, 2H), 2.60 (s, 3H), 7.55 (m, 1H), 8.25 (m, 1H), 8.65 (m, 1H), 8.80 (br, 1H), 9.15 (m, 1H) |
| 53 | CD$_3$CN: 2.7 (s, 3H), 3.7 (dq. 2H), 4.6 (dt, 2H), 6.8 (br, 1H), 7.45 (m, 1H), 8.2 (d, 1H), 8.65 (d, 1H), 9.1 (s, 1H) |
| 54 | d$_6$-DMSO: 1.1-1.2 (m, 2H), 2.50 (s, 3H), 2.80 (m, 1H), 4.75 (m, 1H),7.55 (m, 1H), 8.25 (m, 1H), 8.30 (m, 1H), 8.65 (m, 1H), 9.11 (m, 1H) |
| 55 | CD$_3$CN: 1.2 (t, 3H), 3.35 (m, 2H), 7 (br, 1H), 7.45 (m, 1H), 8.2 (s, 1H), 8.25 (d, 1H), 8.65 (m, 1H), 9.1 (s, 1H) |
| 57 | CD$_3$CN: 2.7 (s, 3H), 3.7 (m, 2H), 6 (t, 1H), 6.9 (br, 1H), 7.45 (m, 1H), 8.25 (d, 1H), 8.65 (m, 1H), 9.1 (s, 1H) |
| 58 | d$_6$-DMSO: 1.2-1.50 (m, 4H), 2.46 (s, 3H), 4.65 (m, 2H), 7.55 (m, 1H), 8.34 (m, 1H), 8.71 (m, 1H), 9.15 (m, 1H) |
| 59 | CD$_3$CN: 2.9 (m, 3H), 6.9 (br, 1H), 7.45 (m, 1H), 8.2 (s, 1H), 8.25 (d, 1H), 8.7 (m, 1H), 9.1 (s, 1H) |
| 60 | d$_6$-DMSO: 2.62 (s, 3H), 4.55 (s, 2H), 6.50 (s, 1H), 7.55 (m, 1H), 8.29 (m, 1H), 8.69 (m, 1H), 8.75 (br, 1H), 8.80 (m, 1H), 9.09 (m, 1H) |
| 198 | d$_6$-DMSO: 1.37-1.40 (m, 2H), 1.60-1.62 (m, 2H), 2.67 (s, 3H), 7.25 (t, 1H), 7.52-7.56 (m, 1H), 8.26-8.29 (m, 1H), 8.67-8.69 (m, 3H), 8.83 (bs, 1H), 9.11 (d, 1H) |

1) Description of Method for Determining the Log P Values (Formic Acid Method)

The log P values reported in the table were determined according to EEC-Directive 79/831 Annex V.A8 by HPLC (High Performance Liquid Chromatography) on a reversed-phase column (C 18).

Temperature: 55° C.

Eluents for the determination in the acidic range (pH 3.4):

Eluent A: acetonitrile+1 ml of formic acid/liter. Eluent B: water+0.9 ml of formic acid/liter.

Gradient: from 10% eluent A/90% eluent B to 95% eluent A/5% eluent B in 4.25 min The calibration was effected with unbranched alkan-2-ones (with 3 to 16 carbon atoms), whose log P values are known (determination of the log P values on the basis of the retention times by linear interpolation between two successive alkanones). The lambda-max values were determined with reference to the UV spectra from 200 nm to 400 nm in the maxima of the chromatographic signals.

Biological Examples

Example No. 1

*Myzus* Test

Solvent: 78.0 parts by weight of acetone
1.5 parts by weight of dimethylformamide
Emulsifier: 0.5 part by weight of alkylaryl polyglycol ether To produce an appropriate active ingredient formulation, 1 part by weight of active ingredient is mixed with the amounts of solvent and emulsifier specified and the concentrate is diluted to the desired concentration with emulsifier-containing water.

Chinese cabbage leaf slices (*Brassica pekinensis*) infested by all stages of the green peach aphid (*Myzus persicae*) are sprayed with an active ingredient formulation of the desired concentration.

After the desired time, the efficacy in % is determined 100% means that all aphids have been killed; 0% means that no aphids have been killed.

In this test, for example, the following compounds of the Preparation Examples have an efficacy of ≥70% at an application rate of 500 g/ha:

Ex. No. 1, 3, 4, 5, 7, 8, 9, 10, 11, 12, 13, 14, 15, 16, 21, 22, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204

Example No. 2

*Phaedon* Test

Solvent: 78.0 parts by weight of acetone
1.5 parts by weight of dimethylformamide
Emulsifier: 0.5 part by weight of alkylaryl polyglycol ether To produce an appropriate active ingredient formulation, 1 part by weight of active ingredient is mixed with the amounts of solvent and emulsifier specified and the concentrate is diluted to the desired concentration with emulsifier-containing water.

Chinese cabbage leaf slices (*Brassica pekinensis*) are sprayed with an active ingredient formulation of the desired concentration and, after drying, populated with larvae of the mustard beetle (*Phaedon cochleariae*).

After the desired time, the efficacy in % is determined. 100% means that all beetle larvae were killed; 0% means that no beetle larvae were killed.

In this test, for example, the following compounds of the Preparation Examples have an efficacy of ≥80% at an application rate of 500 g/ha:

Ex. No. 39, 75

Example No. 3

*Spodoptera frugiperda* Test

Solvent: 78.0 parts by weight of acetone
1.5 parts by weight of dimethylformamide
Emulsifier: 0.5 part by weight of alkylaryl polyglycol ether To produce an appropriate active ingredient formulation, 1 part by weight of active ingredient is mixed with the amounts of solvent and emulsifier specified and the concentrate is diluted to the desired concentration with emulsifier-containing water.

Maize leaf slices (*Zea mays*) are sprayed with an active ingredient formulation of the desired concentration and, after drying, populated with caterpillars of the armyworm (*Spodoptera frugiperda*).

After the desired time, the efficacy in % is determined. 100% means that all caterpillars were killed; 0% means that no caterpillar was killed.

In this test, for example, the following compounds of the Preparation Examples have an efficacy of ≥80% at an application rate of 500 g/ha:
Example No. 39

Example No. 4

*Tetranychus* Test, OP-Resistant

Solvent: 78.0 parts by weight of acetone
1.5 parts by weight of dimethylformamide
Emulsifier: 0.5 part by weight of alkylaryl polyglycol ether To produce an appropriate active ingredient formulation, 1 part by weight of active ingredient is mixed with the amounts of solvent and emulsifier specified and the concentrate is diluted to the desired concentration with emulsifier-containing water.

Common bean leaf slices (*Phaseolus vulgaris*) infested by all stages of the two-spotted spider mite (*Tetranychus urticae*) are sprayed with an active ingredient formulation of the desired concentration.

After the desired time, the efficacy in % is determined 100% means that all spider mites were killed; 0% means that no spider mites were killed.

In this test, for example, the following compounds of the Preparation Examples have an efficacy of ≥80% at an application rate of 100 g/ha:
Ex. No. 53

Example No. 5

*Meloidogyne* Test

Solvent: 80 parts by weight of acetone

To produce an appropriate active ingredient formulation, 1 part by weight of active ingredient is mixed with the amount of solvent stated and the concentrate is diluted to the desired concentration with water.

Vessels are filled with sand, active ingredient solution, *Meloidogyne incognita* egg/larvae suspension and lettuce seeds. The lettuce seeds germinate and the plants develop. Galls develop on the roots.

After the desired time, the nematicidal action is determined on the basis of gall formation in %. 100% means that no galls were found; 0% means that the number of galls on the treated plants corresponds to that of the untreated control.

In this test, for example, the following compounds of the Preparation Examples have an efficacy of ≥80% at an application rate of 20 ppm:
Ex. No. 98, 200

Example No. 6

*Boophilus microplus* Test

Solvent: dimethyl sulphoxide

To produce an appropriate active ingredient formulation, 1 part by weight of active ingredient is mixed with the amount of solvent stated and the concentrate is diluted to the desired concentration with water.

The active ingredient solution is injected into the abdomen (*Boophilus microplus*); the animals are transferred to dishes and stored in a climate-controlled room. The action is monitored by the laying of fertile eggs.

After the desired time, the efficacy in % is determined. 100% means that no ticks have laid fertile eggs.

In this test, for example, the following compounds of the Preparation Examples have an efficacy of ≥80% at an application rate of 20 μg/animal:
Ex. No. 35, 53, 67, 70, 85, 87, 111

Example No. 7

*Lucilia cuprina* Test

Solvent: dimethyl sulphoxide

To produce an appropriate active ingredient formulation, 1 part by weight of active ingredient is mixed with the amount of solvent stated and the concentrate is diluted to the desired concentration with water.

Vessels containing horse meat which has been treated with the active ingredient formulation of the desired concentration are populated with *Lucilia cuprina* larvae.

After the desired time, the kill rate in % is deter 100% means that all larvae were killed; 0% means that no larvae were killed.

In this test, for example, the following compounds of the Preparation Examples have an efficacy of ≥80% at an application rate of 100 ppm:
Ex. No. 35

The invention claimed is:

1. A compound of formula (I)

(I)

in which
$G^1$ is CH and
$G^2$ is

(A)

$R^1$ is hydrogen or alkyl and
$G^3$ is $C(=O)NR^2R^3$,
in which
$R^2$ is a radical from the group of hydrogen, $C_1$-$C_6$-alkyl, $C_1$-$C_6$-haloalkyl, $C_1$-$C_4$-alkoxy, $C_1$-$C_4$-haloalkoxy, $C_2$-$C_4$-alkenyl, $C_1$-$C_4$-alkoxy-$C_1$-$C_4$-alkyl, optionally halogen-substituted $C_1$-$C_4$-alkylcarbonyl, optionally halogen-substituted $C_1$-$C_4$-alkoxycarbonyl, and optionally halogen-substituted $C_3$-$C_6$-cycloalkylcarbonyl,
and
$R^3$ is $C_1$-$C_6$-haloalkyl;
or a salt or N-oxide thereof.

2. A compound of claim 1, or a salt or N-oxide thereof wherein $R^1$ is methyl.

3. A compound of claim 1, or a salt or N-oxide thereof wherein $R^2$ is methyl.

4. A compound of claim 1, or a salt or N-oxide thereof wherein $R^3$ is $CH_2CF_2CH_3$.

5. A compound of claim 1, wherein $R^1$ is methyl, $R^2$ is methyl, and $R^3$ is $CH_2CF_2CH_3$.

6. A compound of claim 1, wherein $R^1$ is methyl, $R^2$ is hydrogen, and $R^3$ is $CH_2CF_2CH_3$.

7. A composition, comprising at least one compound of the formula (I) ng to claim 1 and one or more extenders, surfactants, or combinations thereof.

* * * * *